US011559474B2

(12) United States Patent
Degeorge et al.

(10) Patent No.: US 11,559,474 B2
(45) Date of Patent: Jan. 24, 2023

(54) HAIR LIGHTENING COMPOSITIONS AND METHODS OF USE

(71) Applicant: L'OREAL, Paris (FR)

(72) Inventors: Michael Degeorge, Old Bridge, NJ (US); Mark Benn, Newark, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/801,425

(22) Filed: Nov. 2, 2017

(65) Prior Publication Data
US 2018/0116930 A1 May 3, 2018

Related U.S. Application Data

(60) Provisional application No. 62/416,413, filed on Nov. 2, 2016.

(51) Int. Cl.
| A61K 8/362 | (2006.01) |
| A61K 8/23 | (2006.01) |
| A61K 8/81 | (2006.01) |
| A61K 8/44 | (2006.01) |
| A61Q 5/12 | (2006.01) |
| A61K 8/73 | (2006.01) |
| A61Q 5/08 | (2006.01) |
| A61Q 5/10 | (2006.01) |
| A61Q 5/06 | (2006.01) |
| A61K 8/22 | (2006.01) |
| A61Q 5/04 | (2006.01) |
| A61K 8/365 | (2006.01) |

(52) U.S. Cl.
CPC .............. *A61K 8/362* (2013.01); *A61K 8/22* (2013.01); *A61K 8/23* (2013.01); *A61K 8/365* (2013.01); *A61K 8/44* (2013.01); *A61K 8/737* (2013.01); *A61K 8/817* (2013.01); *A61Q 5/04* (2013.01); *A61Q 5/065* (2013.01); *A61Q 5/10* (2013.01); *A61Q 5/12* (2013.01); *A61K 2800/48* (2013.01); *A61K 2800/882* (2013.01); *A61Q 5/08* (2013.01)

(58) Field of Classification Search
None
See application file for complete search history.

(56) References Cited

U.S. PATENT DOCUMENTS

| 4,855,130 | A | * | 8/1989 | Konrad | ..................... A61K 8/31 424/70.1 |
| 5,951,969 | A | | 9/1999 | Golinski et al. | |
| 5,985,803 | A | | 11/1999 | Rizvi et al. | |
| 6,358,502 | B1 | * | 3/2002 | Tanabe | ................... A61K 8/362 424/70.1 |
| 9,095,518 | B2 | | 8/2015 | Pressly et al. | |
| 9,326,926 | B2 | | 5/2016 | Pressly et al. | |
| 9,597,273 | B2 | | 3/2017 | Pressly et al. | |
| 2004/0235700 | A1 | * | 11/2004 | Legrand | ............... A61K 8/8158 510/302 |
| 2007/0107142 | A1 | | 5/2007 | Nguyen et al. | |
| 2012/0031423 | A1 | * | 2/2012 | Wood | ....................... A61K 8/64 132/208 |
| 2013/0149274 | A1 | | 6/2013 | Nguyen et al. | |
| 2014/0171354 | A1 | | 6/2014 | Miralles et al. | |
| 2015/0004117 | A1 | | 1/2015 | Tan et al. | |
| 2015/0004119 | A1 | | 1/2015 | Tan et al. | |
| 2015/0034119 | A1 | | 2/2015 | Pressly et al. | |
| 2015/0037270 | A1 | | 2/2015 | Pressly et al. | |
| 2015/0037271 | A1 | | 2/2015 | Pressly et al. | |
| 2015/0290101 | A1 | | 10/2015 | Pressly et al. | |
| 2015/0328102 | A1 | | 11/2015 | Pressly et al. | |
| 2016/0175238 | A1 | | 6/2016 | Shin et al. | |
| 2016/0235649 | A1 | | 8/2016 | Streuli | |
| 2018/0353404 | A1 | * | 12/2018 | Nocker | .................. A61K 8/362 |

FOREIGN PATENT DOCUMENTS

| DE | 1220969 | 11/1964 |
| JP | 63154611 A | 6/1988 |
| JP | 2015086211 A | 5/2015 |
| KR | 10-2001-0039848 A | 7/2001 |

OTHER PUBLICATIONS

"Final Written Decision for U.S. Pat. No. 9,668,954 B2", Paper 78, Jul. 30, 2019, Case PGR2018-00025.
Olaplex with relaxers, Olaplex™, pp. 1-2, Apr. 11, 2017, https://olaplex.es/olaplex-with-relaxers/.
Relaxers, Resource Library, Olaplex Education, pp. 1-2, Apr. 11, 2017, https://help.olaplex.com/detail/relaxers.

* cited by examiner

*Primary Examiner* — Nicole P Babson
(74) *Attorney, Agent, or Firm* — The Marbury Law Group, PLLC

(57) ABSTRACT

The present disclosure relates to hair care compositions such as hair treatment compositions and hair lightening compositions, methods for treating hair (e.g., lightening hair), and to kits comprising the compositions. The components of the hair treatment compositions may be included in hair lightening compositions and used to lighten and/or color hair. The hair treatment compositions typically include: (a) one or more polycarboxylic acids, and/or a salt thereof; (b) one or more amino acids, and/or a salt thereof; and optionally (c) one or more cationic conditioning agents. The hair lightening compositions further include (d) one or more bleaching agents.

19 Claims, 5 Drawing Sheets

HAIR LIGHTENING COMPOSITIONS AND METHODS OF USE

CROSS-REFERENCE TO RELATED APPLICATION

This application claims the benefit of U.S. Provisional Application No. 62/416,413, filed Nov. 2, 2016.

FIELD OF THE DISCLOSURE

The present disclosure relates to compositions and methods for treating hair, kits comprising the compositions, and methods for using the compositions.

BACKGROUND

It is known that consumers desire to use cosmetic and care compositions that enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve chemical treatment of the hair.

The process of changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening, generally requires the use of compositions that comprise at least one oxidizing agent.

Lightening or lifting the color of the hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

In general, hair lightening or color lifting compositions and hair dyeing compositions possess an alkalinity such that these compositions have a pH value of above 7, typically being at pH 9 and above, and may generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effective alter the shape of the hair, these chemical treatments can damage the hair fibers and/or irritate the scalp. Thus, in order to reduce or avoid the drawbacks mentioned above, as well as to improve the cosmetic performance of the compositions, the use of new and additional components and novel combinations of ingredients are continuously sought.

However, the choice of components or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can treat the hair, e.g. lift the color of hair and/or deposit color onto hair in an efficient manner, while providing other cosmetic advantages such as shine, conditioning, fiber strength, and/or a healthy appearance to the hair, but avoiding or minimizing damage to the hair.

Further, both natural and sensitized or chemically treated hair can contain several kinds of negatively charged moieties, for example, carboxylates (resulting from the hydrolysis of amino acids and thioester bonds) and/or sulfonates (resulting from the oxidation of disulfide bonds). These negatively charged moieties can degrade the cosmetic properties of the hair. Moreover, when hair is chemically treated or damaged, the disulfide bonds in hair (disulfide linkages between two cysteine units) can be reduced or broken, resulting in the formation of thiol groups and/or cysteic acid.

Thus, one objective of the disclosure is to provide novel compositions that can provide advantageous effects such as strengthening of the hair fiber, protecting hair fibers from damage or further damage, enhanced properties such as softness, shine, conditioning, healthy appearance, while at the same time, providing desired effects such as coloring, lightening, straightening, relaxing, and/or shaping.

SUMMARY OF THE DISCLOSURE

The present disclosure relates to compositions and methods for treating hair, in particular human hair of the head. The compositions and methods are unique because, in addition to lightening the hair, they dramatically improve the quality and durability of the lightened hair. Damage during chemical treatment (lightening/bleaching process) is minimized and/or compensated for due to the use of a treatment composition that may protects the keratin fibers of the hair.

The treatment compositions of the instant disclosure typically include (a) one or more polycarboxylic acids, and/or a salt thereof; (b) one or more amino acids, and/or a salt thereof; and optionally (c) one or more cationic conditioning agents. The treatment compositions may be separate compositions that are combined with one or more bleaching agents prior to use, or it can be part of a single hair lightening composition (a composition having one or more bleaching agents).

Useful polycarboxylic acids include, but are not limited to, dicarboxylic acids and/or tricarboxylic acids, a salt thereof, and a mixture thereof. Non-limiting of dicarboxylic acids include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, a salt thereof, and a mixture thereof. In some cases, particularly useful dicarboxylic acids include malonic acid and/or maleic acid, and/or salts thereof. Non-limiting examples of tricarboxylic acids include citric acid, isocitric acid, trimesic acid, aconitric acid (cis and/or trans), and propane-1,2,3-tricarboxylic acid, and salts thereof. In some cases, a particularly useful tricarboxylic acid is citric acid, and/or a salt thereof.

Useful amino acids include, but are not limited to, aliphatic amino acids such as glycine, alanine, valine, leucine, and isoleucine, and salts thereof. In some cases, glycine and/or a salt thereof is particularly useful.

Useful cationic conditioning agents, if present, include, but are not limited to, monoalkyl quaternary amines, dialkyl quaternary amines, and polyquaternium compounds.

The instant disclosure relates to hair lightening compositions that include the components of the hair treatment compositions mentioned above. For instance, the instant disclosure relates to hair lightening compositions comprising: (a) one or more polycarboxylic acids, and/or a salt thereof; (b) one or more amino acids, and/or a salt thereof; (c) optionally, one or more cationic conditioning agents; and (d) one or more bleaching agents. Non-limiting examples of polycarboxylic acids, amino acids, and conditioning agents are provided above.

Useful bleaching agents include, but are not limited to peroxides, persulfates, perborates percarbonates, alkali metal bromates, ferricyanides, peroxygenated salts, and mixtures thereof.

In some cases, the hair lightening compositions further include one or more oils, which may be one or more ester oils, silicone oils, fluoro oils, vegetable oils, animal oils, hydrocarbon-based oils, and mixtures thereof. Additionally, the hair lightening compositions may optionally include one or more thickening agents. Useful thickening agent include, but are not limited to, carboxylic acid polymers, crosslinked polyacrylate polymers, polyacrylamide polymers, polysaccharides, and gums, in particular guar gum.

The hair treatment compositions and/or the hair lightening compositions are often anhydrous or essentially anhydrous.

The hair lightening composition may optionally include colorants and/or dyes. Useful colorants are those that are stable in the hair lightening compositions. These colorants can be used, for example, to impart toning and coloring to hair. Non-limiting colorants include pigments, liposoluble dyes, direct dyes, oxidative dye precursors, nacreous pigments, pearling agents, leuco dyes, optical lightening colorants, natural colorants and optically-variable pigments. Couplers may also be incorporated into the hair lightening compositions.

The instant disclosure additionally relates to kits comprising the hair treatment compositions and/or hair lightening compositions. For example, kits can include a hair treatment composition that is separate from a hair lightening composition. The kits can optionally include an aqueous developer composition (often comprising a peroxide such as hydrogen peroxide). Alternatively, kits can include a hair lightening composition of the instant disclosure (a single compositions including the components of the treatment compositions and bleaching agent(s)) and a include a separate aqueous developer composition. Typically, the aqueous developer compositions include one or more peroxides, such as hydrogen peroxide. Optionally, the kits may include an additional composition comprising one or more hair conditioning agents and/or one or one or more hair coloring agents.

Finally, the instant disclosure relates to methods for lightening and/or coloring hair; and to methods for protecting and/or improving the appearance of hair, wherein the methods involve application of a composition described herein to the hair; allowing the composition to remain on the hair for a sufficient amount of time for processing (about 1 min. to about 60 min.); and rinsing the compositions from the hair.

BRIEF DESCRIPTION OF THE DRAWINGS

Implementations of the present technology will now be described, by way of example only, with reference to the attached figure, wherein.

Figure 1:
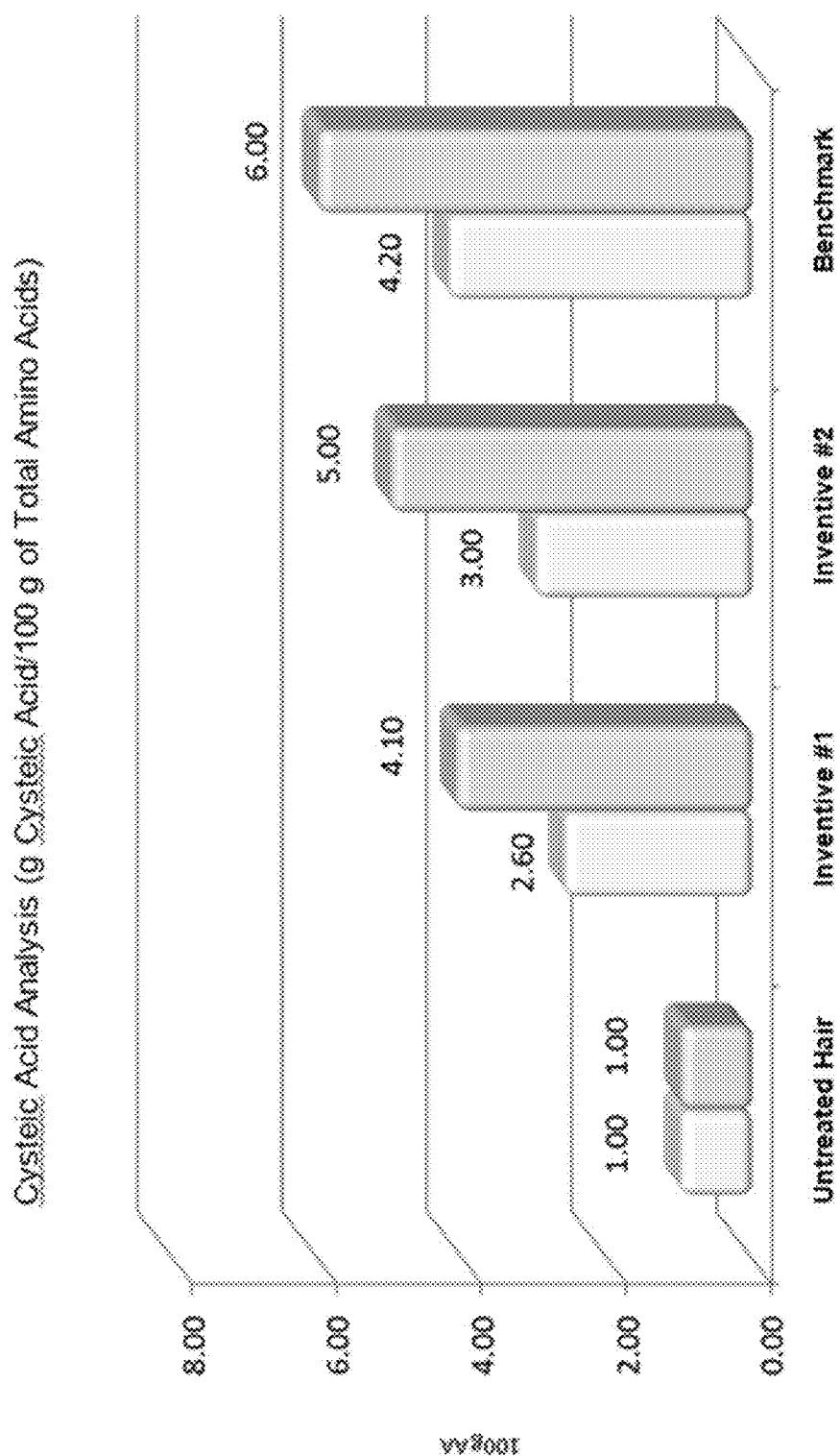
FIG. 1 is a graph comparing cysteic acid analysis results for hair treated with compositions according to the instant disclosure and hair treated with a comparative (benchmark) composition.
Figure 2:
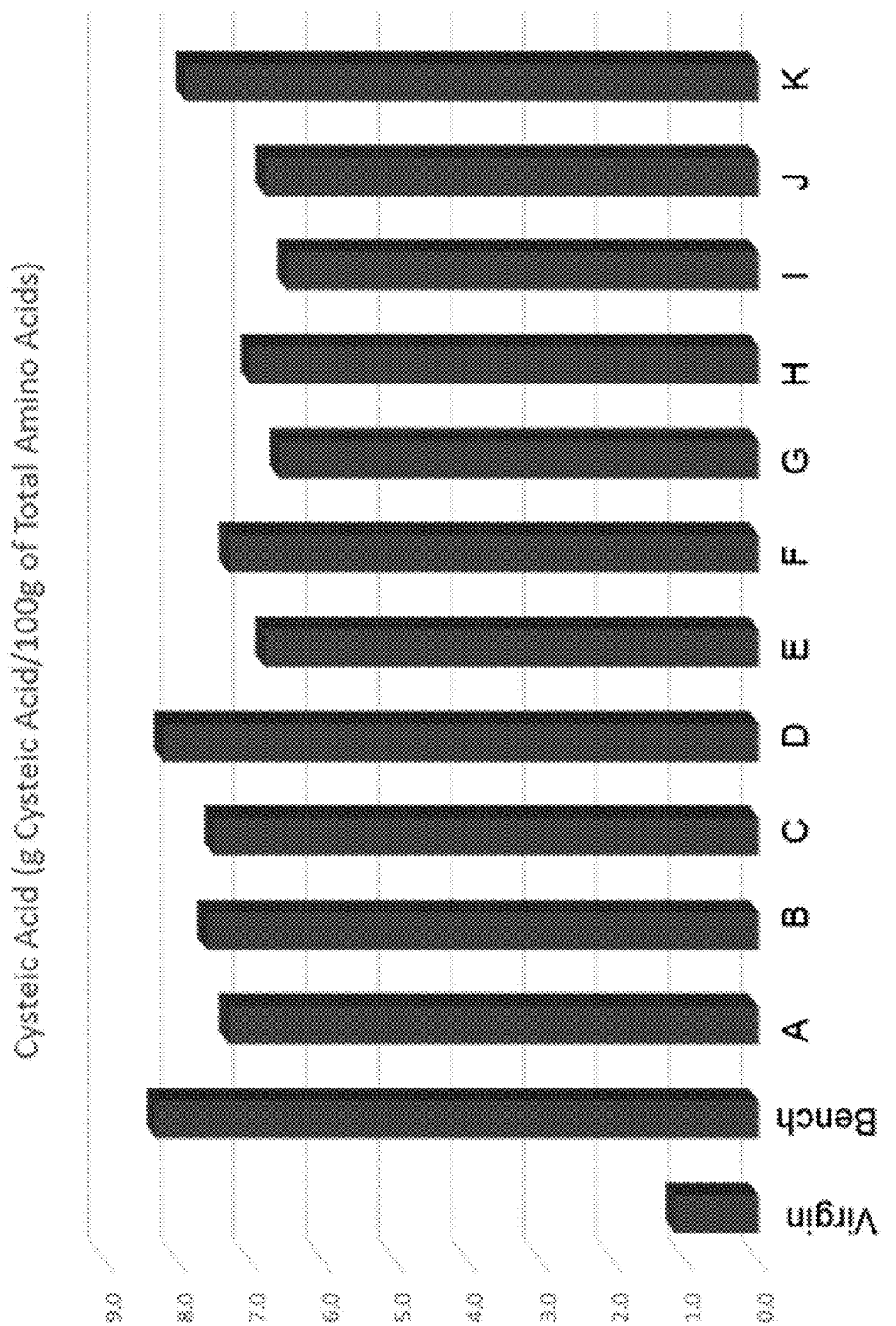
FIG. 2 is another graph comparing cysteic acid analysis results for hair treated with additional compositions according to the instant disclosure and hair treated with a comparative (benchmark) composition.
Figure 3:
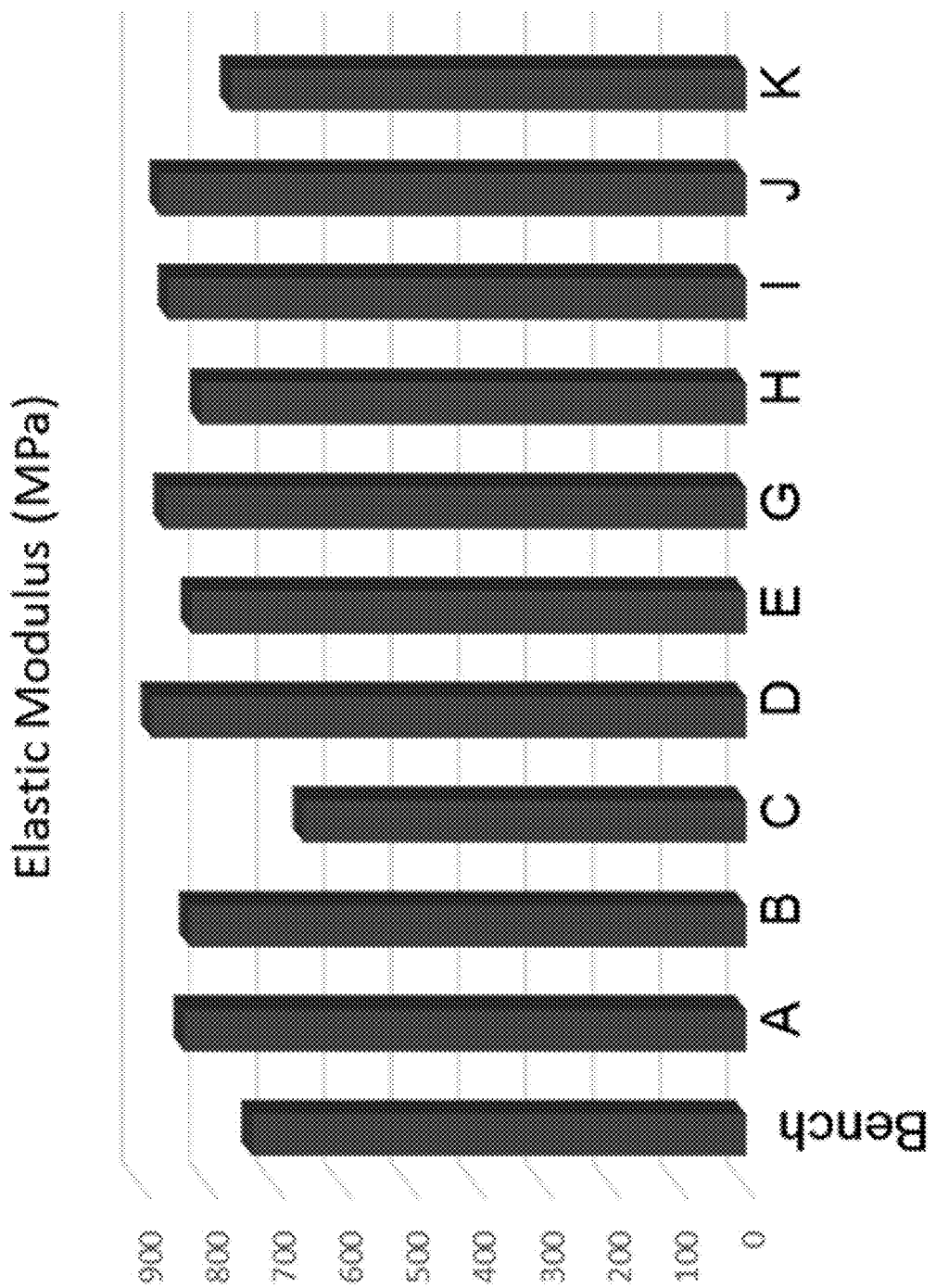
FIG. 3 is a graph comparing elastic modulus testing results for hair treated with compositions according to the instant disclosure and hair treated with a comparative (benchmark) composition.
Figure 4:
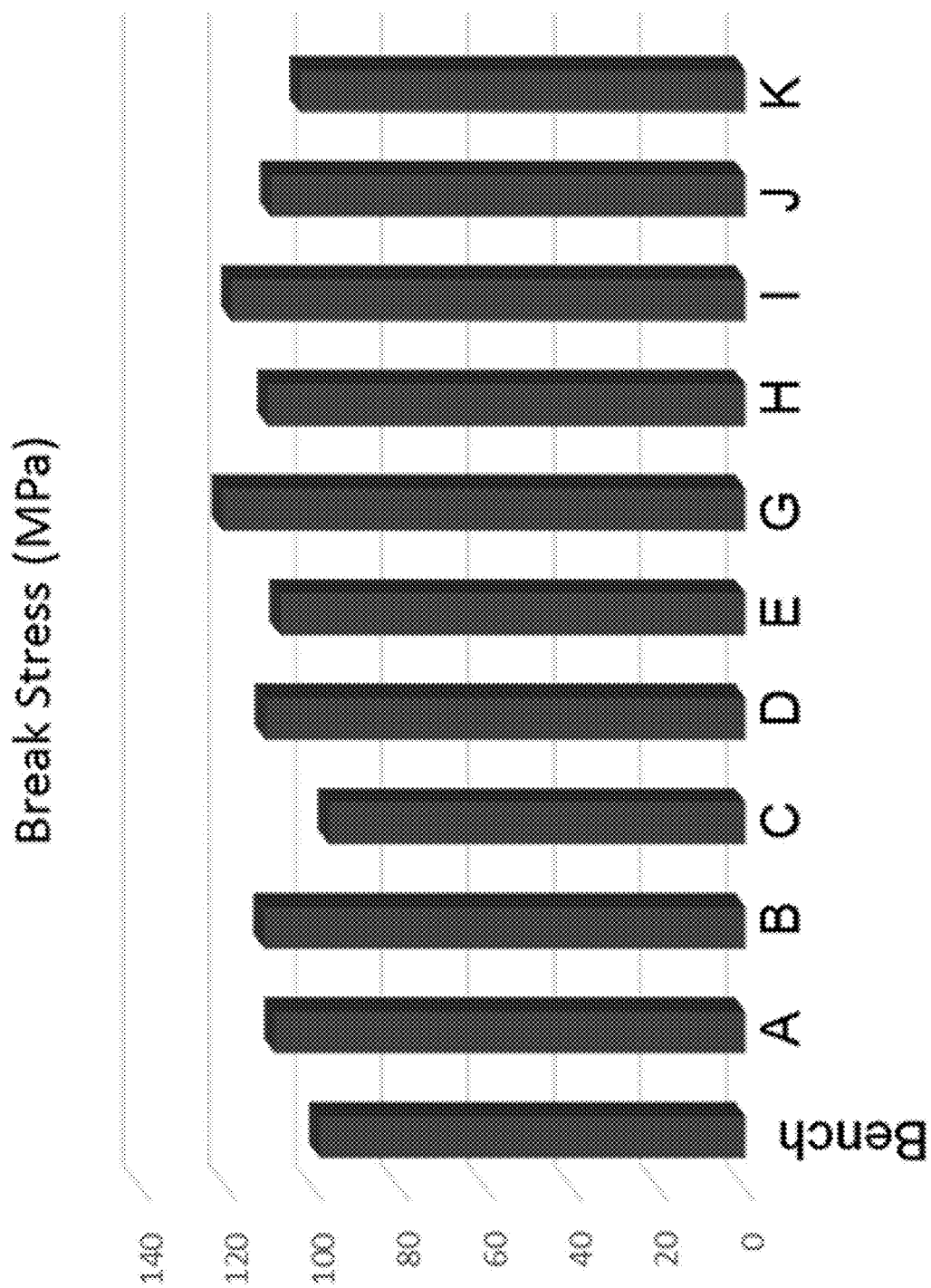
FIG. 4 is a graph comparing break stress testing results for hair treated with compositions according to the instant disclosure and hair treated with a comparative (benchmark) composition.
Figure 5:
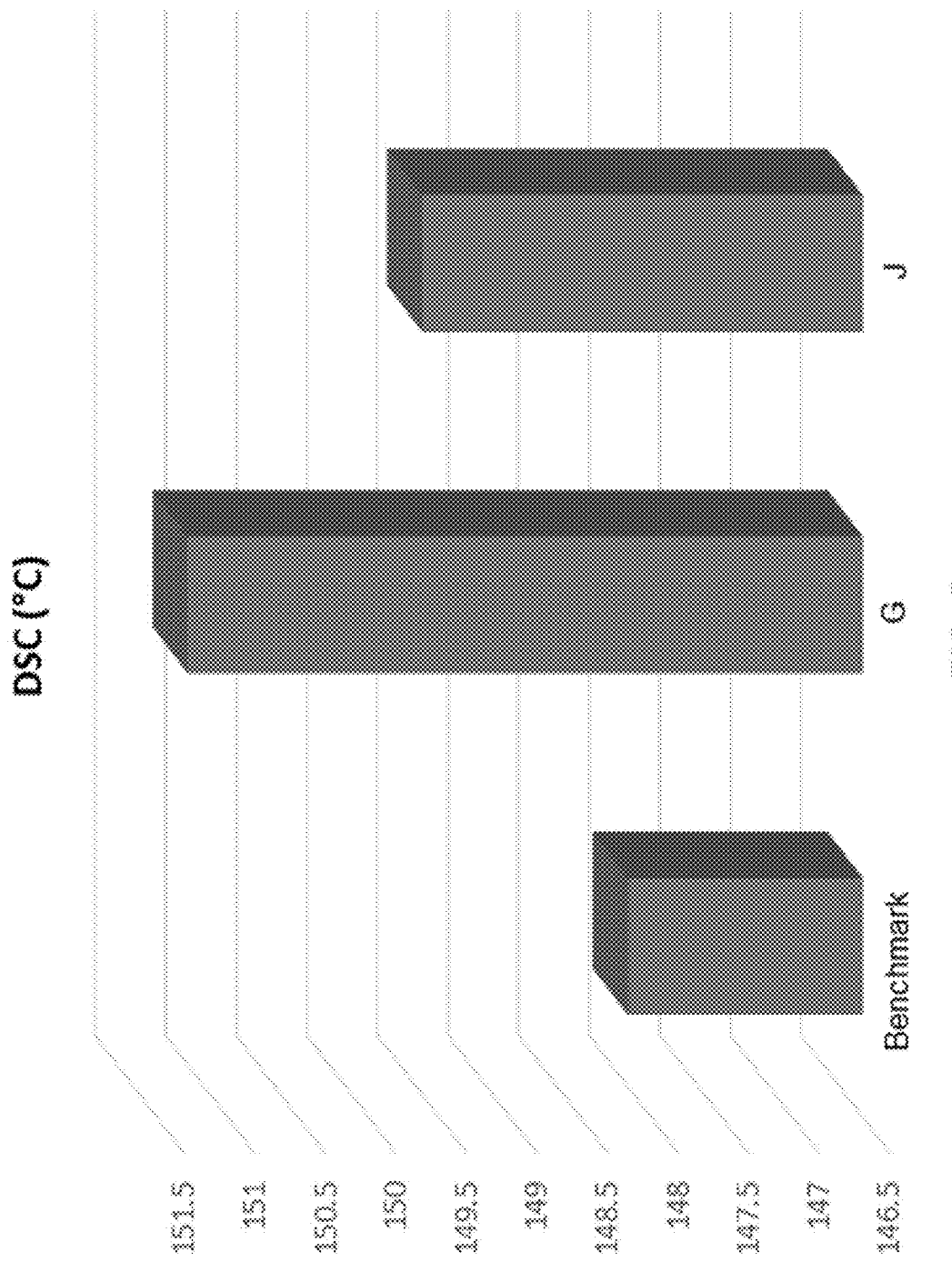
FIG. 5 is a graph comparing Differential Scanning calorimetry (DCS) results for hair treated with compositions according to the instant disclosure and hair treated with a comparative (benchmark composition).

It should be understood that the various aspects are not limited to the arrangements and instrumentality shown in the drawings.

DETAILED DESCRIPTION OF THE DISCLOSURE

The instant disclosure relates to hair care compositions that are useful for lightening and/or coloring hair. The compositions are unique in that they reduce the amount of damage caused to the hair due to chemical processing (bleaching). A hair treatment composition relates to a composition that strengthens hair and/or reduces the damage incurred to the hair by chemical processing including the bleaching and/or coloring of the hair. Treated hair fibers (hair treated with the compositions) have desirable cosmetic properties such as improved gloss, improved combability, and improved strength and elasticity. Successful treatment of the hair can be determined by, for example, by cystic acid analysis.

The hair treatment compositions of the instant disclosure typically include:
(a) one or more polycarboxylic acids and/or a salt thereof;
(b) one or more amino acids, and/or a salt thereof; and
(c) optionally, one or more cationic conditioning agents.

The amounts of the three components of the hair treatment compositions can vary and will depend on the other components (and the amounts of the other components) in the hair treatment compositions, if present. Nonetheless, in general, regardless of the other components in the hair treatment composition, the ratio of the (a) one or more polycarboxylic acids to the (b) one or more amino acids is about 2:1 to about 10:1. Furthermore, the ratio of the (a) one or more polycarboxylic acids to the (b) one or more amino acids may be about 3:1 to about 9:1, about 4:1 to about 8:1, or about 5:1 to about 6:1.

In general, the ratio of the (a) one or more polycarboxylic acids to the (c) one or more cationic conditioning agents is about 1:1 to about 8:1, if one or more cationic conditioning agents are present. However, the ratio of the (a) one or more polycarboxylic acids to the (c) one or more cationic conditioning agents may be about 2:1 to about 7:1, about 2:1 to about 6:1, about 2:1 to about 5:1, about 3:1 to about 7:1, about 3:1 to about 6:1, about 3:1 to about 5:1, or about 3:1 to about 4:1.

In general the ratio of the (b) one or more amino acids to the (c) one or more cationic conditioning agents is 0.1:1 to about 5:1. However, the ratio of the (b) one or more amino acids to the (c) one or more cationic conditioning agents may be about 0.1:1 to about 2:1, about 0.1:1 to about 1:1, about 0.2:1 to about 3:1, about 0.2:1 to about 2:1, about 0.2:1 to about 1:1, about 0.5:1 to about 3:1, about 0.5:1 to about 2:1, or about 0.5:1 to about 1:1.

The instant disclosure also relates to hair lightening compositions that include the components of the hair treatment compositions mentioned above. A treatment composition can be added directly to a hair lightening composition to derive a ready-to-use hair lightening composition. For example, the hair treatment compositions can be added to a hair lightening composition, mixed, and the mixture immediately (within 1 to 60 minutes) applied to hair. Alternatively, the hair lightening composition can already include the components of the hair treatment composition (no separate packing and mixing is required). Accordingly, the instant disclosure relates to hair lightening compositions comprising:

(a) one or more polycarboxylic acids, and/or a salt thereof;
(b) one or more amino acids, and/or a salt thereof;
(c) optionally, one or more cationic conditioning agents; and
(d) one or more bleaching agents.

The ratios for components (a), (b), and (c) discussed above with respect to the treatment compositions can apply to the hair lightening compositions.

In some cases, the one or more polycarboxylic acids are di-, tri-, and/or tetra-carboxylic acids. Non-limiting examples of dicarboxylic acids include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, and salts thereof. Non-limiting examples of tricarboxylic acids include citric acid, isocitric acid, trimesic acid, aconitric acid (cis and/or trans), and propane-1,2,3-tricarboxylic acid, and salts thereof. A non-limiting example of a tetracarboxylic acid is butane tertracarboxylic acid, and a salt thereof. In some instances, the polycarboxylic acid may be selected from the group consisting of maleic acid, malonic acid, citric acid, a salt thereof, and a mixture thereof.

The total amount of the one or more polycarboxylic acids, and/or salt thereof, can vary, but is typically about 0.1 to about 10 wt. %, based on the total weight of the hair lightening composition. In some cases, the total amount of the one or more polycarboxylic acids, and/or salt thereof is from about 0.1 to about 8 wt. %, about 0.1 to about 6 wt. %, about 0.1 to about 5 wt. %, about 0.5 to about 10 wt. %, 0.5 to about 8 wt. %, about 0.5 to about 6 wt. %, about 0.5 to about 5 wt. %, about 1 to about 10 wt. %, about 1 to about 8 wt. %, about 1 to about 6 wt. %, or about 1 to about 5 wt. %.

Amino acids are well known. An "amino acid" is any organic compound having both an amino group and a carboxylic acid group. In some cases, the one or more amino acids are aliphatic amino acids, for example, those selected from the group consisting of glycine, alanine, valine, leucine, isoleucine, a salt thereof, and a mixture thereof. Glycine and/or a salt of glycine is particularly useful in some instances. The total amount of the one or more amino acids, and/or salts thereof, can vary but typically the hair lightening compositions comprise about 0.01 to about 5 wt. % of the one or more amino acids, and/or salt thereof, based on the total weight of the hair lightening composition. In some cases, the total amount of the one or more amino acids and/or salts thereof, is about 0.01 to about 4 wt. %, about 0.01 to about 3 wt. %, about 0.01 to about 2 wt. %, about 0.1 to about 5 wt. %, about 0.1 to about 4 wt. %, about 0.1 to about 3 wt. %, or about 0.1 to about 2 wt. %.

Cationic conditioning agents are well known. Non-limiting examples of the one or more cationic conditioning agents useable in the compositions of the instant disclosure include monoalkyl quaternary amines, dialkyl quaternary amines, and polyquaternium compounds. In some cases, polyquaternium compounds are used and in some cases the polyquaternium compounds are polyquaternium polymers. One type of polyquaternium polymers that are useful include quaternized copolymer(s) of dimethyldiallylammonium and acrylic acid, such as for example, polyquaternium-22. The total amount of the one or more cationic conditioning agents may vary but when present are typically in an amount of about 0.01 to about 10 wt. %, based on the total weight of the hair lighting composition. In some cases, the total amount of the one or more cationic conditioning agents is about 0.01 to about 8 wt. %, about 0.01 to about 6 wt. %, about 0.01 to about 5 wt. %, 0.01 to about 4 wt. %, about 0.01 to about 3 wt. %, about 0.1 to about 10 wt. %, 0.1 to about 8 wt. %, about 0.1 to about 6 wt. %, about 0.1 to about 5 wt. %, about 0.1 to about 4 wt. %, about 0.1 to about 3 wt. %, about 0.5 to about 10 wt. %, about 0.5 to about 8 wt. %, about 0.5 to about 6 wt. %, about 0.5 to about 5 wt. %, about 0.5 to about 4 wt. %, or about 0.5 to about 3 wt. %.

Bleaching agents are well known. Non-limiting examples of bleaching agents include peroxides, persulfates, perborates percarbonates, alkali metal bromates, ferricyanides, peroxygenated salts, and mixtures thereof. Bleaching agents that may also be used include at least one redox enzyme such as laccases, peroxidases, and 2-electron oxidoreductases, such as uricase, where appropriate in the presence of their respective donor or co-factor. In some cases, the one or more bleaching agents are persulfates, for example, one or more of sodium persulfate, potassium persulfate, and ammonium persulfate. The total amount of the one or more bleaching agents can vary but is typically about 20 to about 80 wt. %, based on the total weight of the hair lightening composition. In some cases, the total amount of the bleaching agent may be from about 20 to about 70 wt. %, about 20 to about 60 wt. %, about 30 to about 80 wt. %, about 30 to about 70 wt. %, about 30 to about 60 wt. %, about 40 to about 80 wt. %, about 40 to about 70 wt. %, about 40 to about 60 wt. %, about 50 to about 80 wt. %, about 50 to about 70 wt. %, or about 50 to about 60 wt. %.

In some cases, the hair lightening compositions include one or more oils. Non-limiting examples of oils include ester oils, silicone oils, fluoro oils, vegetable oils, animal oils, hydrocarbon-based oils, and mixtures thereof. In some instances, hydrocarbon-based oils, such as mineral oil, can be included. The total amount of the one or more oils can vary but is typically about 0.1 to about 10 wt. %, based on the total weight of the hair lightening composition. In some cases, the total amount of the one or more oils is about 0.1 to about 8 wt. %, about 0.1 to about 6 wt. %, about 0.1 to about 5 wt. %, about 0.5 to about 10 wt. %, about 0.5 to about 8 wt. %, about 0.5 to about 5 wt. %, about 1 to about 10 wt. %, about 1 to about 8 wt. %, about 1 to about 6 wt. %, or about 1 to about 5 wt. %.

The hair lightening composition can also optionally include one or more thickening agents. Thickening agents are well known. Nonetheless, non-limiting examples of thickening agents include carboxylic acid polymers, cross-linked polyacrylate polymers, polyacrylamide polymers, polysaccharides, and gums. More specific, non-limiting examples of thickening agents include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hydroxylpropyl guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof. In some cases, the one or more thickening agents include a cross-linked polyacrylate polymer, for example, acrylates/C10-30 alkylacrylate crosspolymer. Furthermore, in some cases the one or more thickening agents include guar gum.

The total amount of the one or more thickening agents can vary but is typically about 0.1 to about 10 wt. %, based on the total weight of the hair lightening composition. In some cases, the total amount of the one or more thickening agents is about 0.01 to about 8 wt. %, about 0.01 to about 6 wt. %, about 0.01 to about 5 wt. %, 0.01 to about 4 wt. %, about 0.01 to about 3 wt. %, about 0.1 to about 10 wt. %, 0.1 to about 8 wt. %, about 0.1 to about 6 wt. %, about 0.1 to about 5 wt. %, about 0.1 to about 4 wt. %, about 0.1 to about 3 wt. %, about 0.5 to about 10 wt. %, about 0.5 to about 8 wt. %, about 0.5 to about 6 wt. %, about 0.5 to about 5 wt. %, about 0.5 to about 4 wt. %, or about 0.5 to about 3 wt. %.

The hair lightening compositions may include one or more anionic surfactants. For instance, the anionic surfactant(s) that may be useful include alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyl-lactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts, and in particular amino alcohol salts, or alkaline-earth metal salts such as the magnesium salt. Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of ($C_6$-$C_{24}$)alkyl sulfates, ($C_6$-$C_{24}$)alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts.

In some cases, the one or more anionic surfactant is selected from the group consisting of sodium oleyl succinate, ammonium lauryl sulphosuccinate, sodium lauryl sulfate, sodium lauryl ether sulfate (also known as sodium laureth sulfate, SLES), sodium lauryl ether sulphosuccinate, ammonium lauryl sulfate (ALS), ammonium lauryl ether sulfate (ammonium laureth sulfate), sodium dodecylbenzene sulphonate, triethanolamine dodecylbenzene sulphonate, sodium cocoyl isethionate, sodium lauryl isethionate, lauryl ether carboxylic acid, sodium N-lauryl sarcosinate, and a mixture thereof. In some instances, preferred anionic surfactants include sodium lauryl sulfate, sodium lauryl ether sulfate, sodium lauryl ether sulphosuccinate, ammonium lauryl sulfate, ammonium lauryl ether sulfate, or a mixture thereof.

The total amount of the one or more anionic surfactants is typically about 0.1 to about 10 wt. %, based on the total weight of the hair lightening composition. In some cases, the total amount of the one or more anionic surfactants is about 0.1 to about 8 wt. %, about 0.1 to about 6 wt. %, about 0.1 to about 5 wt. %, about 0.1 to about 3 wt. %, or about 0.5 to about 2 wt. %, based on the total weight of the hair lightening composition.

The hair lightening compositions often include one or more alkalizing agents. The term "alkalizing agent" means an ingredient that is capable imparting alkalinity (e.g. a pH of greater than 7) to the hair lightening composition. The hair lightening compositions typically have an alkaline pH (a pH of greater than 7), e.g., a pH of about 8 to about 11, or about 8 to about 10. Suitable alkalizing agents include ammonium hydroxide, metal hydroxides, alkanolamines, sodium silicate, metal carbonates, such as magnesium carbonate, sodium metasilicate, and a mixture thereof. Suitable metal hydroxides and carbonates include alkali metal and alkaline earth metal hydroxides or carbonates. Examples of such metal hydroxides include sodium, potassium, lithium, calcium, magnesium and so on. A common alkaline earth metal hydroxide is sodium hydroxide. Suitable alkanolamines include mono-, di-, and trialkanolamines such as monoethanolamine (MEA), diethanolamine (DEA), triethanolamine (TEA), 2-aminobutanol, aminoethyl propanediol, aminomethyl propanediol, bis-hydroxyethyl tromethamine, diethanolamine, diethyl ethanolamine, diisopropanolamine, dimethylamino methylpropanol, dimethyl MEA, isopropanolamine, methylethanolamine, mixed isopropanolamines, triisopropanolamine, tromethamine, and mixtures thereof. A particularly preferred alkanolamine is MEA. In some instances, the hair lightening compositions include one or more alkalizing agents selected from the group consisting of ammonium hydroxide, sodium silicate, sodium metasilicate, monoethanolamine, and a mixture thereof.

The total amount of the one or more alkalizing agents can vary but is typically about 1 to about 40 wt. %, based on the total weight of the hair lightening composition. In some instances, the total amount of the one or more alkalizing agents is about 1 to about 35 wt. %, about 1 to about 30 wt. %, about 1 to about 25 wt. %, about 5 to about 40 wt. %, about 5 to about 35 wt. %, about 5 to about 30 wt. %, about 5 to about 25 wt. %, about 10 to about 40 wt. %, about 10 to about 35 wt. %, about 10 to about 30 wt. %, or about 10 to about 25 wt. %, based on the total weight of the hair lightening composition.

One or more fillers may optionally be included in the hair lightening compositions. Non-limiting examples of fillers include starches, maltodextrins, calcium silicates, perlites, zeolites, polylactic acids, silicas, polyamide powders, polyvinylpyrrolidones, dextrose, oligosaccharides, celluloses, diatomite, diatomaceous earth, talc, clays, silicon dioxide, magnesium silicates (i.e. talc powder), clays, and a mixture thereof. In some instances, the one or more fillers comprises one or more alkali metal salts of fatty acids and/or organic base salts of fatty acids, for example, sodium stearate, zinc laurate, magnesium stearate, magnesium myristate, zinc stearate, ammonium stearate, ammonium oleate, ammonium nonanoate, sodium palmitate, potassium stearate, potassium palmitate, sodium myristate, aluminum monostearate, and a mixture thereof.

The total amount of the one or more fillers may vary but is typically about 1 to about 40 wt. %, based on the total weight of the hair lightening composition. In some instances, the total amount of the one or more fillers is about 1 to about 35 wt. %, about 1 to about 30 wt. %, about 1 to about 25 wt. %, about 5 to about 40 wt. %, about 5 to about 35 wt. %, about 5 to about 30 wt. %, about 5 to about 25 wt. %, about 10 to about 40 wt. %, about 10 to about 35 wt. %, about 10 to about 30 wt. %, or about 10 to about 25 wt. %, based on the total weight of the hair lightening composition.

The hair treatment compositions and the hair lightening compositions of the instant disclosure are often anhydrous or essentially anhydrous. The term "essentially anhydrous" means that the composition is either completely free of water or contains no appreciable amount of water, for example, no more than 3% by weight, or no more than 2% by weight, or no more than 1% by weight, based on the total weight of the composition.

A non-limiting example of a hair lightening composition according to the instant disclosure includes: (a) about 0.1 to about 10 wt. % of maleic acid; (b) about 0.01 to about 5 wt. % of one or more aliphatic amino acids selected from the group consisting of glycine, alanine, valine, leucine, isoleucine, and mixtures thereof; (c) about 0.01 to about 10 wt. % of one or more cationic conditioning agents; (d) about 20 to about 80 wt. % of one or more persulfates selected from the group consisting of sodium persulfate, potassium persulfate, ammonium persulfate, and mixtures thereof; (e) about 0.1 to about 10 wt. % of one or more oils; and (f) about 0.1 to about 10 wt. % of one or more thickening agents.

In one embodiment, the instant disclosure relates to essentially anhydrous hair lightening compositions that include:
about 0.1 to about 10 wt. %, about 1 to about 8 wt. %, or about 1 to about about 5 wt. % of about one or more polycarboxylic acids selected from the group consisting of maleic acid, malonic acid, citric acid, a salt thereof, and a mixture thereof;
about 0.01 to about 5 wt. %, about 0.05 to about 4 wt. %, or about 0.1 to about 3 wt. % of one or more aliphatic amino acids selected from the group consisting of glycine, alanine, valine, leucine, isoleucine, a salt thereof, and a mixture thereof; and in particular, glycine and/or a salt thereof;
optionally, one or more cationic conditioning agents;
about 20 to about 80 wt. %, about 30 to about 70, or about 35 to about 65 wt. % of one one or more bleaching agents, for example, one or more peroxides, persulfates, perborates percarbonates, alkali metal bromates, ferricyanides, peroxygenated salts, or a mixture thereof; and in particular one or more persulfates selected from the group consisting of potassium persulfate, sodium persulfate, ammonium persulfate, or a mixture thereof;
about 0.1 to about 10 wt. %, about 0.5 to about 8 wt. %, or about 1 to about 5 wt. % of one or more oils, for example, one or more ester oils, silicone oils, fluoro oils, vegetable oils, animal oils, hydrocarbon-based oils, or mixtures thereof; and particularly one or more hydrocarbon-based oils such as mineral oil;
about 0.1 to about 10 wt. %, about 0.1 to about 6 wt. %, or about 0.5 to about 5 wt. % of one or more thickening agents, for example, one or more thickening agents selected from the group consisting of acacia, agar, algin, alginic acid, ammonium alginate, amylopectin, calcium alginate, calcium carrageenan, carrageenan, dextrin, gelatin, gellan gum, guar gum, guar hydroxypropyltrimonium chloride, hydroxylpropyl guar hydroxypropyltrimonium chloride, hectorite, hyaluroinic acid, hydrated silica, hydroxypropyl chitosan, hydroxypropyl guar, karaya gum, locust bean gum, natto gum, potassium alginate, potassium carrageenan, propylene glycol alginate, sclerotium gum, sodium carboyxmethyl dextran, sodium carrageenan, tragacanth gum, xanthan gum, acrylates/C10-30 alkylacrylate crosspolymer, and mixtures thereof; and in particular, guar gum;
about 0.1 to about 10 wt. %, about 0.1 to about 6 wt. %, or about 0.5 to about 5 wt. % of one or more anionic surfactants, for example, one or more anionic surfactants selected from the group consisting of sodium oleyl succinate, ammonium lauryl sulphosuccinate, sodium lauryl sulfate, sodium lauryl ether sulfate, sodium lauryl ether sulphosuccinate, ammonium lauryl sulfate (ALS), ammonium lauryl ether sulfate, sodium dodecylbenzene sulphonate, triethanolamine dodecylbenzene sulphonate, sodium cocoyl isethionate, sodium lauryl isethionate, lauryl ether carboxylic acid, sodium N-lauryl sarcosinate, and a mixture thereof; and
about 1 to about 40 wt. %, about 5 to about 35 wt. %, or about 10 to about 25 wt. % of one or more alkalizing agents, for example one or more alkalizing agents selected from the group consisting of ammonium hydroxide, sodium silicate, sodium metasilicate, monoethanolamine, and a mixture thereof.
optionally, about 1 to about 40 wt. %, about 5 to about 35 wt. %, or about 10 to about 25 wt. % of one or more fillers, for example, one or more alkali metal salts of fatty acids and/or organic base salts of fatty acids, such as sodium stearate, zinc laurate, magnesium stearate, magnesium myristate, zinc stearate, ammonium stearate, ammonium oleate, ammonium nonanoate, sodium palmitate, potassium stearate, potassium palmitate, sodium myristate, aluminum monostearate, or a mixture thereof.

Further to the above, in some cases, the hair coloring compositions of the instance disclosure are essentially anhydrous hair coloring compositions that include:
- about 0.1 to about 10 wt. %, about 1 to about 8 wt. %, or about 1 to about about 5 wt. % of about one or more polycarboxylic acids selected from the group consisting of maleic acid, malonic acid, citric acid, a salt thereof, and a mixture thereof; in particular citric acid and/or a salt thereof;
- about 0.01 to about 5 wt. %, about 0.05 to about 4 wt. %, or about 0.1 to about 3 wt. % of glycine and/or a salt thereof;
- about 20 to about 80 wt. %, about 30 to about 70, or about 35 to about 65 wt. % of one or more one or more persulfates, for example, one or more persulfates selected from the group consisting of potassium persulfate, sodium persulfate, ammonium persulfate, or a mixture thereof;
- about 0.1 to about 10 wt. %, about 0.5 to about 8 wt. %, or about 1 to about 5 wt. % of one or more oils, for example, one or more ester oils, silicone oils, fluoro oils, vegetable oils, animal oils, hydrocarbon-based oils, or mixtures thereof; and particularly one or more hydrocarbon-based oils such as mineral oil;
- about 0.1 to about 10 wt. %, about 0.1 to about 6 wt. %, or about 0.5 to about 5 wt. % of one or more thickening agents, for example, one or more thickening agents selected from the group consisting of carrageenan, gelatin, gellan gum, guar gum, guar hydroxypropyltrimonium chloride, hydroxylpropyl guar hydroxypropyltrimonium chloride, hydroxypropyl guar, sclerotium gum, tragacanth gum, xanthan gum, and mixtures thereof; and in particular, xanthan gum;
- about 0.1 to about 10 wt. %, about 0.1 to about 6 wt. %, or about 0.5 to about 5 wt. % of one or more anionic surfactants selected from the group consisting of sodium oleyl succinate, ammonium lauryl sulphosuccinate, sodium lauryl sulfate, sodium lauryl ether sulfate, sodium lauryl ether sulphosuccinate, ammonium lauryl sulfate (ALS), ammonium lauryl ether sulfate, sodium dodecylbenzene sulphonate, triethanolamine dodecylbenzene sulphonate, sodium cocoyl isethionate, sodium lauryl isethionate, lauryl ether carboxylic acid, sodium N-lauryl sarcosinate, and a mixture thereof; and
- about 1 to about 40 wt. %, about 5 to about 35 wt. %, or about 10 to about 25 wt. % of one or more alkalizing agents selected from the group consisting of ammonium hydroxide, sodium silicate, sodium metasilicate, monoethanolamine, and a mixture thereof.
- optionally, about 1 to about 40 wt. %, about 5 to about 35 wt. %, or about 10 to about 25 wt. % of one or more fillers, for example, one or more alkali metal salts of fatty acids and/or organic base salts of fatty acids, such as sodium stearate, zinc laurate, magnesium stearate, magnesium myristate, zinc stearate, ammonium stearate, ammonium oleate, ammonium nonanoate, sodium palmitate, potassium stearate, potassium palmitate, sodium myristate, aluminum monostearate, or a mixture thereof.

Further to the above, and even more specifically, hair coloring compositions of the instance disclosure are essentially anhydrous hair coloring compositions that include:
- about 0.1 to about 10 wt. %, about 1 to about 8 wt. %, or about 1 to about about 5 wt. % of maleic acid, malonic acid, citric acid, a salt thereof, or a mixture thereof;
- about 0.01 to about 5 wt. %, about 0.05 to about 4 wt. %, or about 0.1 to about 3 wt. % of glycine and/or a salt thereof;
- about 20 to about 80 wt. %, about 30 to about 70, or about 35 to about 65 wt. % of potassium persulfate, sodium persulfate, ammonium persulfate, or a mixture thereof;
- about 0.1 to about 10 wt. %, about 0.5 to about 8 wt. %, or about 1 to about 5 wt. % of one or more oils, for example, one or more ester oils, silicone oils, fluoro oils, vegetable oils, animal oils, hydrocarbon-based oils, or mixtures thereof; and particularly one or more hydrocarbon-based oils such as mineral oil;
- about 0.1 to about 10 wt. %, about 0.1 to about 6 wt. %, or about 0.5 to about 5 wt. % of guar gum;
- about 0.1 to about 10 wt. %, about 0.1 to about 6 wt. %, or about 0.5 to about 5 wt. % of one or more anionic surfactants selected from the group consisting of sodium lauryl sulfate, sodium lauryl ether sulfate, sodium lauryl ether sulphosuccinate, ammonium lauryl sulfate (ALS), ammonium lauryl ether sulfate, and a mixture thereof; and
- about 1 to about 40 wt. %, about 5 to about 35 wt. %, or about 10 to about 25 wt. % of one or more alkalizing agents selected from the group consisting of sodium silicate, sodium metasilicate, and a mixture thereof;
- about 1 to about 40 wt. %, about 5 to about 35 wt. %, or about 10 to about 25 wt. % of one or more fillers, for example, one or more alkali metal salts of fatty acids and/or organic base salts of fatty acids, such as sodium stearate, zinc laurate, magnesium stearate, magnesium myristate, zinc stearate, ammonium stearate, ammonium oleate, ammonium nonanoate, sodium palmitate, potassium stearate, potassium palmitate, sodium myristate, aluminum monostearate, or a mixture thereof.

The above hair lightening compositions may optionally include one or more cationic conditioning polymers. Alternatively, cationic conditioning polymers may be excluded, i.e., the hair lightening compositions may be free or essentially free of cationic conditioning polymers.

The instant disclosure additionally relates to kits comprising the hair treatment compositions and/or hair lightening compositions. For example, kits can include a hair structuring compositions that are separate from a hair lightening compositions that are separate from an optional aqueous developer composition. Alternatively, kits can include the hair lightening compositions of the instant disclosure (comprising the components of the treatment compositions and bleaching agent(s)) and a separate aqueous developer composition. Typically, the aqueous developer compositions include one or more peroxides, such as hydrogen peroxide. Optionally, the kits may include an additional composition comprising one or more hair conditioning agents and/or one or hair coloring agents.

Finally, the instant disclosure relates to methods for lightening and/or coloring hair; and to methods for protecting and/or improving the appearance of hair, wherein the methods involve applications of the compositions described herein to the hair; allowing the compositions to remain on the hair for a sufficient amount of time for processing; and rinsing the compositions from the hair.

More exhaustive but non-limiting lists of components that are useful in the compositions of the instant disclosure are presented below.

Polycarboxylic Acids

The polycarboxylic acid may be chosen especially from linear, branched and/or cyclic, saturated or unsaturated, or even aromatic, polycarboxylic acids, containing 2 to 50, especially 2 to 40 carbon atoms, in particular 3 to 36, or even 3 to 18, 4 to 12 carbon atoms, or even 5 to 10 carbon atoms; the acid comprising at least two carboxylic groups COOH, or from 2 to 4 COOH groups; and possibly comprising 1 to 10 or 1 to 6 identical or different heteroatoms, chosen from O, N and S; and/or possibly comprising at least one perfluoro radical chosen from —$CF_2$— (divalent) or —$CF_3$.

In some cases, the said polycarboxylic acid is saturated, linear and aliphatic and contains 2 to 36 carbon atoms, especially 3 to 18 carbon atoms or even 4 to 12 carbon atoms; or alternatively is aromatic and contains 8 to 12 carbon atoms. In some cases, it may comprise 2 to 4 COOH groups.

The cyclic anhydride of a polycarboxylic acid may especially correspond to one of the following formulae:

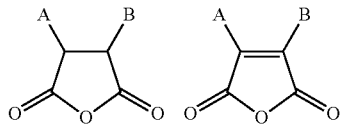

in which the groups A and B are, independently of each other: a hydrogen atom, a saturated or unsaturated, linear, branched and/or cyclic aliphatic, or alternatively aromatic, carbon-based radical; containing 1 to 16 carbon atoms, especially 2 to 10 carbon atoms or even 4 to 8 carbon atoms, especially methyl or ethyl, or alternatively A and B taken together form a saturated or unsaturated, or even aromatic, ring comprising in total 5 to 14, especially 5 to 10 or even 6 to 7 carbon atoms. In some cases, A and B represent a hydrogen atom or together form an aromatic ring containing in total 6 to 10 carbon atoms.

Among the polycarboxylic acids or anhydrides thereof that may be used, mention may be made, alone or as a mixture, of: dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid and fatty acid dimers (especially of $C_{36}$); tricarboxylic acids such as cyclohexanetricarboxylic acid, trimellitic acid, 1,2,3-benzenetricarboxylic acid and 1,3,5-benzenetricarboxylic acid, tetracarboxylic acids such as butanetetracarboxylic acid and pyromellitic acid, cyclic anhydrides of these acids and especially phthalic anhydride, trimellitic anhydride, maleic anhydride and succinic anhydride.

Mention may also be made of polycarboxylic acids chosen, alone or as a mixture, from:

(i) polycarboxylic acids containing a saturated or unsaturated, linear or branched chain comprising at least one heteroatom chosen from O, N and/or S, especially 1 to 10 identical or different heteroatoms, and/or comprising at least one perfluoro radical —$CF_2$— or —$CF_3$ and moreover containing at least 2 carboxylic groups COOH and especially 2 to 4 COOH groups; and/or a cyclic anhydride of such a polycarboxylic acid; and/or (ii) saturated or unsaturated, or even aromatic, heterocyclic polycarboxylic acids, comprising at least one heteroatom chosen from O, N and/or S, especially 1 to 10, or even 1 to 4, identical or different heteroatoms, and at least 2 carboxylic groups COOH and especially 2 to 4 COOH groups; and/or a cyclic anhydride of such a polycarboxylic acid; and/or (iii) sugar-based polycarboxylic acids, which may be obtained especially by oxidation of an aldose, and comprising at least 2 carboxylic groups COOH and especially 2 or 3 COOH groups; and/or a cyclic anhydride of such a polycarboxylic acid; and/or (iv) itaconic anhydride and 1,4,5,8-naphthalenetetracarboxylic acid 1,4-monoanhydride; and/or (v) polycarboxylic (including heterocyclic) amino acids, i.e. polycarboxylic acids containing a saturated or unsaturated, linear, branched and/or cyclic chain, optionally comprising at least one heteroatom chosen from O, N and/or S, especially 1 to 10 identical or different heteroatoms, and/or optionally comprising at least one perfluoro radical —$CF_2$— or —$CF_3$; and also comprising at least one primary, secondary or tertiary amine function (especially $NR^1R^2$ with $R^1$ and $R^2$, independently of each other, chosen from H and $C_1$-$C_{12}$ alkyl), especially 1 to 3 identical or different amine functions, and moreover containing at least 2 carboxylic groups COOH, especially 2 to 4 COOH groups; and/or a cyclic anhydride of such a polycarboxylic acid.

Mention may be made most particularly, alone or as a mixture, of the following dicarboxylic acids: (i) 2,2'[1,5-pentanediylbis(thio)]bis-acetic acid 6,6'-[(1,2-dioxo-1,2-ethanediyl)diimino]bis-hexanoic acid 2,2'-sulfinylbis-acetic acid 4,13-dioxo-3,5,12,14-tetraazahexadecanedioic acid poly(ethylene glycol)disuccinate, especially of mass 250-600 poly(ethylene glycol)bis(carboxymethyl) ether, especially of mass 250-600 poly[oxy(1,2-dicarboxy-1,2-ethanediyl)], especially of DP<10 8-[(carboxymethyl)amino]-8-oxooctanoic acid 2,2'-[methylenebis(sulfonyl)]bis-acetic acid 4,4'-(1,6-hexanediyldiimino)bis[4-oxobutanoic acid] 4,9-dioxo-3,5,8,10-tetraazadodecanedioic acid 4-[(1-carboxyethyl)amino]-4-oxobutanoic acid 6-[(3-carboxy-1-oxopropyl)amino]hexanoic acid N,N'-(1,6-dioxo-1,6-hexanediyl)bis-glycine N,N'-(1,6-dioxo-1,6-hexanediyl)bis-phenylalanine N,N'-(1,3-dioxo-1,3-propanediyl)bis-glycine 4,4'-[(1,4-dioxo-1,4-butanediyl)diimino]bis-butanoic acid 4,4'-[(1,6-dioxo-1,6-hexanediyl)diimino]bis-butanoic acid 6,6'-[1,6-hexanediylbis(iminocarbonylimino)]bis-hexanoic acid N-benzoyl-S-(carboxymethyl)cysteine N,N'-(2,2,3,3-tetrafluoro-1,4-dioxo-1,4-butanediyl)bis-glycine N,N'-(2,2,3,3-tetrafluoro-1,4-dioxo-1,4-butanediyl)bis-alanine 4,4'-[(2,2,3,3-tetrafluoro-1,4-dioxo-1,4-butanoic acid N,N'-(1,5-dioxo-1,5-pentanediyl)bis-glycine N,N'-(1,9-dioxo-1,9-nonanediyl)bis-glycine N,N'-(1,10-dioxo-1,10-decanediyl) bis[N-methyl]glycine bis(3-carboxypropyl)ester of propanedioic acid 7,16-dioxo-6,8,15,17-tetraazadocosanedioic acid N-benzoyl-N-(2-carboxyethyl)glycine [2-[(2-carboxymethyl)amino]-2-oxoethyl]benzenepropanoic acid [2-[(2-carboxyethyl)amino]-2-oxoethyl]benzenepropanoic acid (ii) 4,7,9,12-tetraoxapentadecanedioic acid 2,3-pyridinedicarboxylic acid 4-pyranone-2,6-dicarboxylic acid 2,5-pyrazinedicarboxylic acid 2,5-pyridinedicarboxylic acid 2,3-benzofurandicarboxylic acid 7-oxabicyclo[2.2.1]heptane-2,3-dicarboxylic acid 3,4-pyridinedicarboxylic acid 2,4-pyridinedicarboxylic acid 3,5-pyridinedicarboxylic acid 2,6-pyridinedicarboxylic acid 1H-imidazole-4,5-dicarboxylic acid 2,3-quinolinedicarboxylic acid 6,6,7,7-tetrafluoro- 3-oxabicyclo[3.2.0]heptane-2,4-dicarboxylic acid 2,6-pyrazinedicarboxylic acid 2,6-dimethyl-3,5-pyridinedicarboxylic acid 1-phenyl-1H-pyrazole-3,4-dicarboxylic acid 2,5-furandicarboxylic acid 3,4-furandicarboxylic acid 1,2,5-thiadiazole-3,4-dicarboxylic acid 1,4-dihydro-1,2,4,5-tetrazine-3,6-dicarboxylic acid 2,3-furandicarboxylic acid 3,4-thiophenedicarboxylic acid 1H-1,2,3-triazole-4,5-dicarboxylic acid 2-methylimidazole-4,5-dicarboxylic acid 2,4-quinolinedicarboxylic acid naphtho[2,1-b]furan-1,2-dicarboxylic acid 3,4-quinolinedicarboxylic acid 7-oxabicyclo[2.2.1]hept-5-ene-2,3-dicarboxylic acid 2,3-quinoxalinedicarboxylic acid 1,4-piperazinedicarboxylic acid 2,5-dimethyl-3,4-furandicarboxylic acid tetrahydro-2,5-thiophenedicarboxylic acid 4-phenyl-3,5-pyridinedicarboxylic acid thieno[3,2-b]thiophene-2,5-dicarboxylic acid 3-methyl-2,4-thiophenedicarboxylic acid naphthostyril-5,6-dicarboxylic acid 3-phenyl-2,4-quinolinedicarboxylic acid 3,4-dimethyl-2,5-dicarboxythiophene 3,4-diphenyl-2,5-thiophenedicarboxylic acid 2,5-diphenyl-3,4-furandicarboxylic acid 7-oxo-7H-benzimidazo[2,1-a]benz[de]isoquinoline-3,4-dicarboxylic acid 2,3-dihydro-1,3-dioxo-1H-benz[de]isoquinoline-6,7-dicarboxylic acid 3,4-bis(phenylmethoxy)-2,5-furandicarboxylic acid 4,4'-bibenzoic acid-2,2'-sulfone 2,7-diphenyl-m-anthrazoline-4,5-dicarboxylic acid 2,4-pyrimidinedicarboxylic acid 2-phenyl-4,5-thiazoledicarboxylic acid 6-phenyl-2,3-pyridinedicarboxylic acid 5,6-dimethyl-2,3-pyrazinedicarboxylic acid 3,7-dibenzothiophenedicarboxylic acid 9-oxo-9H-xanthene-1,7-dicarboxylic acid 2-(1,1-dimethylethyl)-H-imidazole-4,5-dicarboxylic acid 6,7-quinolinedicarboxylic acid 6-methyl-2,3-pyridinedicarboxylic acid 4,5-pyrimidinedicarboxylic acid 2-methyl-3,4-furandicarboxylic acid 1,2-indolizinedicarboxylic acid 2,8-dibenzothiophenedicarboxylic acid 3,6-pyridazinedicarboxylic acid 1,10-phenanthroline-2,9-dicarboxylic acid 1,4,5,6-tetrahydro-5,6-dioxo-2,3-pyrazinedicarboxylic acid 3,4-dimethoxy-2,5-furandicarboxylic acid 2-ethyl-4,5-imidazoledicarboxylic acid 2-propyl-1H-imidazole-4,5-dicarboxylic acid 4-phenyl-2,5-pyridinedicarboxylic acid 4,5-pyridazinedicarboxylic acid 1,4,5,8-tetrahydro-1,4:5,8-diepoxynaphthalene-4a,8a-dicarboxylic acid 5,5-dioxide-2,8-dibenzothiophenedicarboxylic acid pyrazolo[1,5-a]pyridine-2,3-dicarboxylic acid 2,3-dihydro-1H-pyrrolizine-1,7-dicarboxylic acid 6-methyl-2,4,5-pyridinetricarboxylic acid pyrrolo[2,1,5-cd]indolizine-5,6-dicarboxylic acid 3,4-bis(2,2,3,3,4,4,4-heptafluorobutyl)-1H-pyrrole-2,5-dicarboxylic acid 6,7,9,10,17,18,20,21-octahydrodibenzo[b,k]-[1,4,7,10,13,16hexaoxacyclooc-tadecin-2,14-dicarboxylic acid 6,7,9,10,17,18,20,21-octahydrodibenzo[b,k]-[1,4,7,10,13,16]hexaoxacyclooctadecin-2,13-dicarboxylic acid 2-methyl-3,4-quinolinedicarboxylic acid 4,7-quinolinedicarboxylic acid 3,5-isoxazoledicarboxylic acid 2-(trifluoromethyl)-3,4-furandicarboxylic acid 5-(trifluoromethyl)-2,4-furandicarboxylic acid 6-methyl-2,4-quinolinedicarboxylic acid 5-oxo-1,2-pyrrolidinedicarboxylic acid 5-ethyl-2,3-pyridinedicarboxylic acid 1,2-dihydro-2-oxo-3,4-quinolinedicarboxylic acid 4,6-phenoxathiindicarboxylic acid 10,10-dioxide 1,9-phenoxathiindicarboxylic acid 3,4-dihydro-2H-1,4-thiazine-3,5-dicarboxylic acid 2,7-di(tert-butyl)-9,9-dimethyl-4,5-xanthenedicarboxylic acid 6-methyl-2,3-quinoxalinedicarboxylic acid 3,7-quinolinedicarboxylic acid 2,5-quinolinedicarboxylic acid 2-methyl-6-phenyl-3,4-pyridinedicarboxylic acid 3,4-dimethylthieno[2,3-b]thiophene-2,5-dicarboxylic acid 3,4-dimethoxythiophene-2,5-dicarboxylic acid 5-methyl-3,4-isoxazoledicarboxylic acid 2,6-bis(aminocarbonyl)-3,5-pyridinedicarboxylic acid 3,5-bis(aminocarbonyl)-2,6-pyrazinedicarboxylic acid 2,3-pyridinedicarboxylic acid 6-(1,1-dimethylethyl)-2-ethyl-3,4-pyridinedicarboxylic acid 3-methyl-5-phenyl-2,4-thiophenedicarboxylic acid 1,2-dihydro-2-oxo-6-phenyl-3,5-pyridinedicarboxylic acid 8-methyl-2,4-quinolinedicarboxylic acid 4-ethyl-2,6-dimethyl-3,5-pyridinedicarboxylic acid 5-(phenoxymethyl)-2,4-furandicarboxylic acid 5-(acetylamino)-3-methyl-2,4-thiophenedicarboxylic acid 2-(4-heptylphenyl)-4,8-quinolinedicarboxylic acid 2,8-bis(4-heptylphenyl)pyrido[3,2-g]quinoline-4,6-dicarboxylic acid 1,2,3,4,6,7,8,9-octahydro-2,8-dioxopyrido[3,2]-quinoline-3,7-dicarboxylic acid 2,8-dimethylpyrido[3,2-g]quinoline-3,7-dicarboxylic acid 5,6-quinolinedicarboxylic acid 6-ethyl-2-methylcinchomeronic acid 2-methyl-6-propylcinchomeronic acid 6-isopropyl-2-methylcinchomeronic acid 6-tert-butyl-2-methylcinchomeronic acid 1,4-dimethyl-7-oxabicyclo[2.2.1]heptane-2,3-dicarboxylic acid 1,2-dihydro-2-oxo-3,8-quinolinedicarboxylic acid 1,2-dihydro-2-oxo-3,6-quinolinedicarboxylic acid 1,2-dihydro-2-oxo-3,7-quinolinedicarboxylic acid 3,7-dimethyl-2,8-diphenylpyrido[3,2-g]quinoline-4,6-dicarboxylic acid 8-methyl-2,3-quinolinedicarboxylic acid 3-[[(1,1-dimethylethyl)amino]sulfonyl]-2,5-thiophenedicarboxylic acid 4-(acetylamino)-2,3-thiophenedicarboxylic acid 2,5-pyridinedicarboxylic acid 2,6-pyridinedicarboxylic acid 2,4-thiophenedicarboxylic acid 2,5-thiophenedicarboxylic acid 1,4-pyran-2,6-dicarboxylic acid (iii) ribaric acid glucaric acid xylaric acid arabinaric acid mannaric acid idaric acid altraric acid L-glucaric acid L-arabinaric acid allaric acid galactaric acid meso-tartaric acid D-glucaric acid L-idaric acid hexaric acid 2,3-dihydroxybutanedioic acid D-tartaric acid D,L-tartaric acid D-glucaric acid tartaric acid tetrahydroxysuccinic acid 2-carboxy-2,3-dideoxy-D-manno-2-octulopyranosonic acid methyl-3-deoxy-D-arabino-2-heptulopyranosaric acid D-lyxo-2-heptulopyranosaric acid 2,6-anhydro-L-glycero-L-galactoheptaric acid (iv) 1,4,5,8-naphthalenetetracarboxylic acid 1,4-monoanhydride itaconic anhydride (v) 1,4-dihydro-4-oxo-2,6-pyridinedicarboxylic acid 2,6-piperidinedicarboxylic acid 1H-pyrrole-3,4-dicarboxylic acid 4-amino-2,6-dicarboxylic acid 1-methyl-1H-pyrazole-3,4-dicarboxylic acid 2,3-piperidinedicarboxylic acid 1-methyl-1H-imidazole-4,5-dicarboxylic acid 2,4-thiazolidinedicarboxylic acid 1-(phenylmethyl)-1H-imidazole-4,5-dicarboxylic acid 5-amino-6-oxo-2,3-piperidinedicarboxylic acid 5-amino-6-oxo-2,4-piperidinedicarboxylic acid 5-amino-6-oxo-2,3-piperidinedicarboxylic acid 5-amino-6-oxo[2S-(2.alpha.,4.beta.,5.alpha.)]-2,4-piperidinedicarboxylic acid (2S,4R)-2,4-pyrrolidinedicarboxylic acid (2S-cis)-2,4-pyrrolidinedicarboxylic acid 2-amino-1H-imidazole-4,5-dicarboxylic acid 2,5-pyrrolidinedicarboxylic acid 4-amino-3,5-isothiazoledicarboxylic acid 1-methyl-1H-pyrazole-3,5-dicarboxylic acid 7-(diethylamino)-2-oxo-2H-1-benzopyran-3,4-dicarboxylic acid 3,4-diethyl-1H-pyrrole-2,5-dicarboxylic acid 1-phenyl-1H-pyrrole-3,4-dicarboxylic acid cis-2,3-piperazinedicarboxylic acid 2,3-piperazinedicarboxylic acid 2,5-piperazinedicarboxylic acid 2,6-piperazinedicarboxylic acid 2-amino-3,5-pyridinedicarboxylic acid 2-methylpyrrole-3,4-dicarboxylic acid 4-(methylamino)-2,6-pyridinedicarboxylic acid 2-amino-6-methyl-3,4-pyridinedicarboxylic acid 5-amino-2-methyl-3,4-pyridinedicarboxylic acid 2-amino-6-methyl-3,5-pyridinedicarboxylic acid 2,5-dimethylpyrrole-3,4-dicarboxylic acid 2,5-dimethylpyrrole-3,4-dicarboxylic acid 2-amino-6-hydroxy-3,5-pyridinedicarboxylic acid 2,4-pyrrolidinedicarboxylic acid 1H-indole-2,4-dicarboxylic acid 1H-indole-2,6-dicarboxylic acid 1H-indole-2,5-dicarboxylic acid 5-phenyl-2,4-pyrrolidinedicarboxylic acid 5-methyl-2,4-pyrrolidinedicarboxylic acid trans-2,4-azetidinedicarboxylic acid cis-2,4-azetidinedicarboxylic acid 3,5-piperidinedicarboxylic acid 2,3-pyrrolidinedicarboxylic acid 2,3-azetidinedicarboxylic acid 3,4-pyrrolidinedicarboxylic acid 2,3-dihydro-6H-1,4-dioxino[2,3-c]pyrrole-5,7-dicarboxylic acid 1H-imidazole-2,4-dicarboxylic acid 1-butyl-1H-pyrrole-2,3-dicarboxylic acid 3-amino-1-oxide-2,4-pyridinedicarboxylic acid 2,3-dihydro-5-phenyl-1H-pyrrolizine-6,7-dicarboxylic acid 3a,4,5,9b-tetrahydro-3H-cyclopenta[c]quinoline-4,6-dicarboxylic acid 3a,4,5,9b-tetrahydro-3H-cyclopenta[c]quinoline-4,8-dicarboxylic acid 2,3-dihydro-1H-imidazole-4,5-dicarboxylic acid 5-amino-6-methyllutidinic acid 1H-indole-3,7-dicarboxylic acid 3,3-dimethyl-2,6-piperidinedicarboxylic acid 1-butyl-2,5-pyrrolidinedicarboxylic acid 1H-indole-4,6-dicarboxylic acid 1-(phenylmethyl)-3,4-pyrrolidinedicarboxylic acid 3-(carboxymethyl)-1H-indole-2,6-dicarboxylic acid 3,4-bis(2,2,2-trifluoroethyl)-1H-pyrrole-2,5-dicarboxylic acid 9-hexyl-9H-carbazole-3,6-dicarboxylic acid 3-methyl-5-(1-piperazinylsulfonyl)-2,4-thiophenedicarboxylic acid 2,3,4,9-tetrahydro-1H-carbazole-5,7-dicarboxylic acid 2,3-dimethyl-1H-indole-4,6-dicarboxylic acid 7-amino-1,4-dihydro-4-oxo-3,6-quinolinedicarboxylic acid 5-amino-3-methyl-2,4-thiophenedicarboxylic acid (m-tolylimino)diacetic acid (o-tolylimino)diacetic acid D-cystathionine phenethyliminodiacetic acid 2-benzyl-2,2'-iminodiacetic acid L-.alpha.-glutamyl-L-alanyl-L-alanine N,N'-dibenzylethylenediaminediacetic acid N-L-.gamma.-glutamyl-D-alanine glycyl-L-glutamylglycine N-(carboxymethyl)-N-(tetrahydro-1,1-dioxido-3-thienyl)glycine N-(2-carboxyethyl)-N-phenyl-beta-alanine N-(carboxymethyl)-N-octylglycine N-(tert-butoxycarbonyl)iminodiacetic acid N-(carboxymethyl)-L-alanine N-(6-aminohexyl)-N-(carboxymethyl)glycine N-(carboxymethyl)-N-tetradecylglycine N-(1-carboxyethyl)-D-alanine N-(carboxymethyl)-D-alanine decyliminodiacetic acid 3,3'-(dimethylhydrazono)bis-propanoic acid N-(carboxymethyl)-N-[2-(2,6-dioxo-4-morpholinyl)ethyl]glycine N-alpha-aspartylglycine N-beta-aspartylglycine N-L-alpha-aspartyl-beta-alanine 3,4-xylylamino-N,N-diacetic acid N-(1-carboxyethyl)alanine N-(carboxymethyl)alanine N,N'-methylenebis-glycine N-(aminomethyl)-N-(carboxymethyl)glycine N-(aminomethyl)-N-(carboxymethyl)glycine 2,2'-(methylhydrazono)bis-acetic acid N-(2-carboxyethyl)-N-(4-methylphenyl)-beta-alanine N-(2-carboxyethyl)-N-(3-methylphenyl)-beta-alanine 3-[(carboxymethyl)amino]alanine D-alpha-aspartyl-D-alanine N-(2-carboxyethyl)-N-(1-oxohexadecyl)-beta-alanine N-(2-carboxyethyl)-N-(1-oxodecyl)-beta-alanine N-(2-carboxyethyl)-N-(1-oxotetradecyl)-beta-alanine amino[(carboxymethyl)thio]acetic acid N,N'-1,6-hexanediylbis-beta-alanine N-(carboxymethyl)-N-phenyl-beta-alanine N-(1-carboxyethyl)-L-alanine L-glutamic acid L-aspartic acid.

Amino Acids

Amino acids are well known. An "amino acid" is any organic compound having both an amino group and a carboxylic acid group. In some cases, the one or more amino acids are N-acyl amino acids. The amino acid can be one of any of the amino acids known in the art. The N-acyl amino acids correspond to the formula:

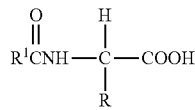

wherein R can be a hydrogen, alkyl (substituted or unsubstituted, branched or straight chain), or a combination of alkyl and aromatic groups. A list of possible side chains of amino acids known in the art are described in Stryer, Biochemistry, 1981, published by W.H. Freeman and Company, which is incorporated herein by reference in its entirety. $R^1$ can be C1 to C30, saturated or unsaturated, straight or branched, substituted or unsubstituted alkyls; substituted or unsubstituted aromatic groups; or mixtures thereof.

In some cases, the N-acyl amino acid compound is selected from the group consisting of N-acyl Phenylalanine, and N-acyl Tyrosine. The amino acid can be the D or L isomer or a mixture thereof. N-acyl Phenylalanine corresponds to the following formula:

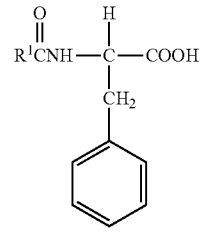

wherein $R^1$ can be C1 to C30, saturated or unsaturated, straight or branched, substituted or unsubstituted alkyls; substituted or unsubstituted aromatic groups; or mixtures thereof. N-acyl Tyrosine corresponds to the following formula:

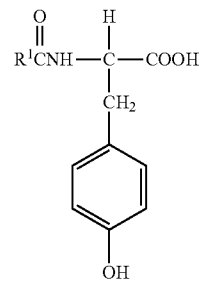

wherein $R^1$ can be C1 to C30, saturated or unsaturated, straight or branched, substituted or unsubstituted alkyls Cationic Conditioning Compounds The cationic conditioning agent employed in the compositions of the present invention can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic conditioning agents are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 in the CTFA Cosmetic Ingredient Dictionary, 3rd Ed., published in 1982 by the Cosmetic Toiletry and Fragrance Association, Inc. (hereafter CTFA Dictionary and CTFA name), is sold under the trademark MERQUAT-100, and is described as having a weight average molecular weight of approximately 100,000. A copolymer reaction product of dimethyldiallylammonium chloride with acrylamide monomers is named Polyquaternium-7 in the CTFA Dictionary, is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the CTFA name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the CTFA name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10 in the CTFA Dictionary. Also useful are quaternized copolymers of hydroxyethylcellulose and dimethyldimethylammonium chloride, having the CTFA name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the CTFA names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the CTFA name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the CTFA name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Bleaching Agents

Bleaching agents may be selected from, for example, peroxides, persulfates, perborates percarbonates, alkali metal bromates, ferricyanides, peroxygenated salts, or a mixture thereof. Bleaching agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the bleaching agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof.

Developer

The hair lightening compositions of the instant disclosure may be combined with a developer composition. A developer composition is typically an aqueous composition that includes one or more oxidizing agents, such as peroxide. Non-limiting examples of oxidizing include those that are water soluble such as peroxygen oxidizing agents. The oxidizing agent may be selected from water-soluble oxidizing agents which are inorganic peroxygen materials capable of yielding hydrogen peroxide in an aqueous solution.

The oxidizing agents may be provided in aqueous solution or as a powder which is dissolved prior to use. Water-soluble oxidizing agents include hydrogen peroxide, inorganic alkali metal peroxides such as sodium peroxide and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. In some cases, hydrogen peroxide, percarbonate, persulphates and combinations thereof, are used in the developer compositions.

The oxidative agent may comprise from about 0.1% to about 40% by weight, from about 1% to about 30% by weight, or from about 2% to about 30% by weight of the developer composition. Another potential oxidizing agent for use herein is a source of peroxymonocarbonate ions. Preferably such a source is formed in situ from a source of hydrogen peroxide and a hydrogen carbonate ion source. This system is particularly effective in combination with a source of ammonia or ammonium ions. Accordingly, any source of these peroxymonocarbonate ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and as an oxidizing agent. Non-limiting examples of carbonate ions, carbamate and hydrocarbonate ions are sodium hydrogen carbonate, potassium hydrogen carbonate, ammonium carbamate, and mixtures thereof.

Oils

The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or organofluorinated oils, volatile or non-volatile silicone oils, fluorosilicone oils and their mixtures.

Non-limiting examples of oils include oils of animal, vegetable or mineral origin, of lanolin, squalene, fish oil, perhydrosqualene, mink oil, turtle oil, soybean oil, grape seed oil, sesame oil, maize oil, rapeseed oil, sunflower oil, cottonseed oil, avocado oil, olive oil, castor seed oil, jojoba seed oil, peanut oil, sweet almond oil, palm oil, cucumber oil, hazelnut oil, apricot kernel oil, wheat germ oil, calophyllum oil, macadamia oil, coconut oil, cereal germ oil, candlenut oil, thistle oil, candelilla oil, safflower oil, shea butter, and their mixtures.

Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

Mention is made, as examples of optionally branched and/or unsaturated fatty acids, of myristic acid, palmitic acid, stearic acid, behenic acid, oleic acid, linoleic acid, linolenic acid or isostearic acid, and their mixtures.

Mention is made, as example of optionally branched and/or unsaturated fatty alcohols, of cetanol, stearyl alcohol, oleyl alcohol, cetyl alcohol, octyldodecanol, and their mixtures.

Mention is made, as examples of esters, of monoesters or polyesters of fatty acids, the linear or branched fatty chain of which includes from 6 to 30 carbon atoms, and of fatty alcohols, the fatty chain of which includes from 3 to 30 carbon atoms, in particular mono- and polyesters of hydroxy acids and of fatty alcohols, esters of benzoic acid and of fatty alcohols, polyesters of polyols, dipentaerythrityl $C_5$-$C_9$ esters, trimethylolpropane polyesters, propylene glycol polyesters, polyesters of hydrogenated castor oil.

Further mention is made of the oils of the group consisting of isononyl isononanoate, stearyl octanoate, isopropyl palmitate, isopropyl myristate, butyl stearate, hexyl laurate, 2-ethylhexyl palmitate, 2-hexyldecyl laurate, 2-octyldecyl palmitate, 2-octyldodecyl myristate, di(2-ethylhexyl) succinate, diisostearyl malate, 2-octyldodecyl lactate, glyceryl triisostearate or diglyceryl triisostearate, octyldodecyl stearoyl stearate (Ceraphyl), cetearyl isononanoate, diisopropyl adipate, caprylic/capric triglyceride, glyceryl tricaprate/caprylate, isocetyl stearoyl stearate, $C_{12}$-$C_{15}$ alkyl benzoates, pentaerythrityl tetraisostearate, dipentaerythrityl pentaisononanoate, bis-diglyceryl polyacyladipate-2, trimethylolpropane triethylhexanoate, propylene glycol dibenzoate, propylene glycol dioctanoate, and mixture thereof.

Mention is made, as example of volatile silicone oils, of hexamethyldisiloxane, dimethicones with a viscosity of between 0.65 and 5 mm$^2$s, octamethylcyclotetrasiloxane, heptamethylhexyltrisiloxane, decamethylcyclopentasiloxane, decamethyltetrasiloxane, octamethyltrisiloxane, dodecamethylcyclohexasiloxane, heptamethyloctyltrisiloxane, and their mixtures.

Mention is made, as example of non-volatile silicone oils, of non-volatile polydialkylsiloxanes; polydimethylsiloxanes comprising pendant alkyl, alkoxy or phenyl groups or alkyl, alkoxy or phenyl groups at the end of the silicone chain, which groups have from 2 to 24 carbon atoms; phenylated silicones, such as those of the phenyl trimethicone type, those of the phenylpropyldimethylsiloxysilicate type or those of the trimethylpentaphenyltrisiloxane type; polysiloxanes modified by fatty acids, in particular $C_8$-$C_{20}$ fatty acids, fatty alcohols, in particular $C_8$-$C_{20}$ fatty alcohols, or polyoxyalkylenes (in particular polyoxyethylene and/or polyoxypropylene); aminated polysiloxanes; polysiloxanes comprising a hydroxyl group; and their mixtures.

Mention is made, as fluorosilicone oils, of fluorinated polysiloxanes comprising a pendant fluorinated group or a fluorinated group at the end of the silicone chain having from 1 to 12 carbon atoms, all or a portion of the hydrogens of which are replaced by fluorine atoms, such as perfluorononyl dimethicone, and their mixtures.

Thickening Agents

The compositions may contain one or more thickeners or viscosity modifying agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

Colorants

Before, after, or simultaneously with the hair lightening composition, a color-altering composition may be used. For example, the color-altering composition may be formed by combining a hair lightening composition according to the instant disclosure, a developer composition (typically comprising hydrogen peroxide) and a colorant. Typically, the coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-I, N,N'-bis(.beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1, 5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1, 5-a]pyrid-5-yl)(2-hydroxyethyl)amino]ethanol, 2-[(3-aminopyrazolo[1,5-a]pyrid-7-yl)(2-hydroxyethyl)amino] ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol--3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers and also the addition salts thereof.

Mention may be made, for example, of 2-methyl-5-aminophenol, 5-N-(.beta.-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyloxy)benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylaminobenzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta.-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:)

 (Va)

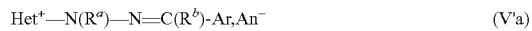 (V'a)

 (VIa)

Ar⁺—N=N-Ar'',An⁻   (VI'a) and

Het⁺- N=N-Ar'-N=N-Ar,An⁻   (VIIa)

in which formulas (Va), (V'a), (VIa), (VI'a) and (VIIa):

Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$) alkoxy Ar'' is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferably with a hydroxyl group;

or alternatively the substituent $R^a$ with a substituent of Het⁺ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An⁻ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

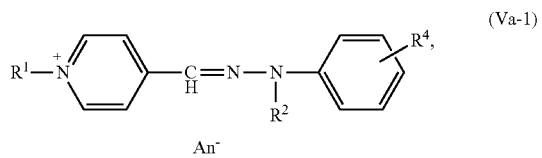
(Va-1)

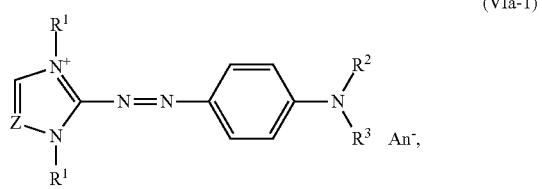
(VIa-1)

wherein in formulae (Va-1) and (VIa-1):

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$)(alkyl)amino optionally substituted on the alkyl group(s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

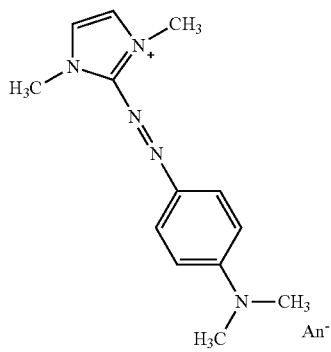
Basic Red 51

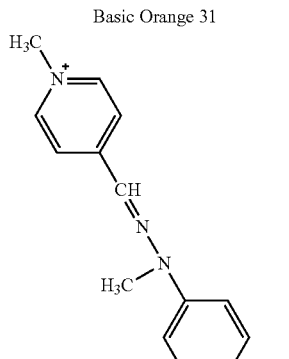
Basic Orange 31

Basic Yellow 87

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.01 wt. % to about 5 wt. %, about 0.15% to about 1 wt. %, or about 1 wt. % to about 3 wt. %, based on the total weight of the composition.

Suitable components, such as those listed above, are included or excluded from the hair care formulations depending on the specific combination of other components, the form of the compositions, and/or the use of the formulation (e.g., hair spray, cream, conditioner, etc.).

Forms

The compositions described herein may be in any suitable physical form. Suitable forms include, but are not limited to low to moderate viscosity liquids, lotions, milks, mousses, sprays, gels, creams, conditioners, and the like.

i. Spray

The compositions described herein for treating hair may be in the form of a spray. The spray typically includes the composition comprising the one or more lactones and a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. Preferably, the spray formulation includes a preservative. In some embodiments, the formulation includes a fragrance. In some cases, the compositions described herein include a surfactant. In some cases, the compositions described herein contain water, fragrance, a preservative, and one or more lactones. In some cases, the compositions described herein contain water, fragrance, a preservative, and one or more lactones. In some cases, the composition comprising one or more lactones contains water, a preservative, fragrance, the one or more lactones, and an anti-static agent. In some cases, the compositions described herein contain water, a preservative, fragrance, the one or more lactones, and a hair conditioning agent. In some cases, the compositions described herein contain water, a preservative, fragrance, the one or more lactones, and a surfactant.

The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

ii. Conditioners

The compositions disclosed herein for treatment of hair may be in the form of a conditioner. The conditioner typically includes the composition comprising the one or more lactones in a suitable carrier. Additionally, the conditioner may include cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

iii. Creams

The compositions disclosed herein for treatment of hair may be in the form of a cream. The cream typically includes one or more lactones in a suitable carrier. The one or more lacatones may be included in any suitable concentration. Typical concentrations of the one or more lactones in the cream range from small amounts such as approximately about 0.01% (wt), at least 0.1% (wt), to large amounts, such as up to about 50% (wt).

Implementation of the present disclosure is provided by way of the following examples. The examples serve to illustrate the technology without being limiting in nature.

EXAMPLE 1

Hair Lightening Compositions

| Component | Ingredient | Benchmark (Commercial Product) | #1 | #2 | #3 |
|---|---|---|---|---|---|
| Polycarboxylic Acid | Maleic Acid | — | 3.3 | 3.3 | 3.3 |
| Amino Acid | Glycine | — | 0.6 | 0.6 | 0.6 |

-continued

| Component | Ingredient | Benchmark (Commercial Product) | #1 | #2 | #3 |
|---|---|---|---|---|---|
| Cationic Conditioning Agent | Polyquaternium-22 | — | 1 | 1 | 1 |
| Bleaching Agents (persulfates) | Potassium persulfate and/or ammonium persulfate | 55 | 55 | 55 | 55 |
| Oil | Mineral Oil | 2 | 2 | 2 | 2 |
| Thickener | Guar Gum | 2 | — | — | — |
|  | Acrylates/C10-30 Alkyl Acrylate Crosspolymer |  | 1 | 1 | 1 |
| Fillers | Sodium Stearate | 10 | 2.5 | 2.5 | 2.5 |
|  | Magnesium Carbonate, Sodium Silicate, and/or Sodium Metasilicate | 28.5 | 32 | 32 | 33 |
| Pigments, Preservatives, Lubricants, Cleansing Agents, Surfactants, Frangrances, etc. | Miscellaneous | 2.5 | ~2.5 | ~2.5 | ~2.5 |

EXAMPLE 2

The hair lightening compositions of Example 1 were mixed with a 40V developer compositions (comprising hydrogen peroxide) in a mix ratio of 1:2 (hair lightening composition:developer composition) and used to treat hair. The hair was subsequently subjected to cysteic acid analysis, which is a measurement showing the degree of damage to the hair. The results are provided in the table below and are graphically shown in FIG. 1.

Cysteic Acid Analysis

| Composition | One Application | Two Applications |
|---|---|---|
| None (Untreated Hair) | 1 | 1 |
| Inventive #1 | 2.6 | 4.1 |
| Inventive #2 | 3 | 5 |
| Comparative | 4.2 | 6 |

EXAMPLE 3

Hair Lightening Compositions

| Component | Description | Benchmark | A | B | C | D | E | F | G | H | I | J | K |
|---|---|---|---|---|---|---|---|---|---|---|---|---|---|
| Polycarboxylic Acid | Citric Acid |  |  | 4.6 |  |  | 4.6 |  | 3.6 | 1.8 |  |  |  |
|  | Malonic Acid |  |  |  | 3.0 | 3.5 |  |  |  |  | 4.0 | 3.0 | 2.0 |
|  | Maleic Acid |  | 3.3 |  |  |  |  | 3.3 |  |  |  |  |  |
| Amino Acid | Glycine |  |  |  |  |  | 0.6 | 0.6 | 0.6 | 0.3 | 0.6 | 0.6 | 0.6 |
| Bleaching Agents | Potassium &/or ammonium persulfate | 54.6 | 52.8 | 52.0 | 52.4 | 52.7 | 52.0 | 52.4 | 53.0 | 53.8 | 52.1 | 52.6 | 53.2 |
| Oil | Mineral Oil | 2.0 | 1.9 | 1.9 | 1.9 | 1.9 | 1.6 | 1.9 | 1.6 | 1.8 | 1.9 | 1.9 | 1.9 |
| Thicken, Agent | Guar Gum | 2 | 2 | 2 | 2 | 2 | 2 | 2 | 2 | 2 | 2 | 2 | 2 |
| Alkalizing Agent | Na silicate, Na metasilicate, and/or Mg Carbonate | 29.3 | 28.3 | 27.9 | 28.1 | 28.2 | 27.9 | 28.2 | 27.9 | 28.6 | 27.9 | 28.2 | 28.5 |
| Fillers | Na stearate | 9.9 | 9.6 | 9.5 | 9.0 | 9.6 | 9.5 | 9.5 | 9.5 | 9.7 | 9.5 | 9.6 | 9.7 |
| Anionic Surfactant | Na Lauryl Sulfate | 1.0 | 1.0 | 1.0 | 1.0 | 1.0 | 1.0 | 1.0 | 1.0 | 1.0 | 1.0 | 1.0 | 1.0 |
| Tris-(hydroxymethyl) aminomethane |  |  |  |  |  | 1.0 |  |  |  |  |  |  |  |
| Misc. | Chelating, colorants, &/or vitamins, etc. | <2 | <2 | <2 | <2 | <2 | <2 | <2 | <2 | <2 | <2 | <2 | <2 |
|  | TOTAL | 100 | 100 | 100 | 100 | 100 | 100 | 100 | 100 | 100 | 100 | 100 | 100 |
| TEST | Cysteic Acid | 8.3 | 7.3 | 7.6 | 7.5 | 8.2 | 6.8 | 7.3 | 6.6 | 7.0 | 6.5 | 6.8 | 7.9 |
| TEST | Elastic Modulus | NA | — | — | — | SB | — | NT | SB | — | SB | SB | — |
| TEST | Break Stress | NA | — | SB | — | SB | — | NT | SB | SB | SB | SB | — |

"SB"—Significantly Better;
"—"—Not Significantly Different;
"NT"—Not Tested;
"N"—Not Applicable (standard)

Cysteic acid analysis is a measurement showing the degree of damage to the hair. Extensive studies of the influence of the cysteine content on the denaturing of the α-helices in keratins have shown, for example, that the melting temperature (transition temperature) of the keratin increases linearly with the cysteine content. The increased stability of the matrix region attributable to the relatively high degree of crosslinking of the high proportion of disulfide bridges in the matrix means that transition of the helices embedded in this matrix is made difficult and, accordingly, results in an increase in the melting temperature. Conversely, a reduction in the melting point and, above all, in the enthalpy of fusion can generally be observed in chemically treated hair.

Elastic modulus (Young's modulus) and break stress are also measurements used to characterize hair and the degree damage to hair. The elastic modulus represents a measure of the hair's spring-like structure (elasticity). Higher elastic modulus shows that the hair is more elastic (less brittle). Break stress represents the force/area needed to break the hair fiber. A higher break stress represents a stronger and stiffer hair fiber.

Differential Scanning Calorimetry (DCS) is a tool that can also be useful for investigating the structural characteristics of hair fibers. Keratin undergoes detectable transformations at various temperatures. Changes in these transformation temperatures can be used to estimate how a particular hair-treatment may impacts hair fibers. In the instant case, DSC was used to measure denaturation temperature ($T_d$). Denaturation temperature ($T_d$) has been used as a representation of the thermal stability of hair fibers, which is influenced, at least in part, by the cross-link density of the matrix (intermediate filament associated proteins, IFAP). Thermal stability ($T_d$) and its relationship in determining the thermal stability of hair fibers is established in the literature.

The results for the cysteic acid testing, elastic modulus, break stress, and DSC for hair treated with the hair lightening compositions from the table above are presented below and graphically shown in FIGS. 2-5.

|   | Cysteic Acid (g Cysteic Acid/100 g of Total Amino Acids) | Elastic Modulus (MPa) | Break Stress (MPa) | DSC (° C.) |
| --- | --- | --- | --- | --- |
| Virgin | 1.2 | N/A | N/A | Not Tested |
| Benchmark | 8.3 | 735 | 98.7 | 148.166 |
| A | 7.3 | 836 | 109.11 | Not Tested |
| B | 7.6 | 828 | 111.58 | Not Tested |
| C | 7.5 | 659 | 96.65 | Not Tested |
| D | 8.2 | 885 | 111.37 | Not Tested |
| E | 6.8 | 825.3 | 107.9 | Not Tested |
| F | 7.3 | Not Tested | Not Tested | Not Tested |
| G | 6.6 | 866.4 | 121.3 | 151.283 |
| H | 7.0 | 812.3 | 110.8 | Not Tested |
| I | 6.5 | 859.7 | 119.1 | Not Tested |
| J | 6.8 | 872.3 | 110.1 | 149.621 |
| K | 7.9 | 766.4 | 103.3 | Not Tested |

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat" (and its grammatical variations) as used herein also refers to contacting keratinous substrates such as hair with the compositions of the present disclosure.

A "rinse-off" product refers to a composition such as a hair care composition that is rinsed and/or washed with water either after or during the application of the composition onto the keratinous substrate, and before drying and/or styling said keratinous substrate. At least a portion of the composition is removed from the keratinous substrate during the rinsing and/or washing.

The term "stable" as used herein means that the composition does not exhibit phase separation and/or crystallization.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair treatment composition comprising:
   (a) citric acid and/or a salt thereof;
   (b) glycine and/or a salt thereof;
   (c) optionally one or more cationic conditioning agents;
   (e) optionally at least one oil;
   (f) optionally at least one thickening agent; and
   (g) one or more anionic surfactants;
   wherein the total amount of compounds chosen from citric acid and salts thereof ranges from about 1 wt % to about 5 wt % based on the total weight of the composition,
   wherein the total amount of compounds chosen from glycine and salts thereof ranges from about 0.1 wt % to about 2 wt % based on the total weight of the composition,
   wherein the composition comprises a total amount of compounds chosen from (a) citric acid and salts thereof and (b) glycine and salts thereof in a weight ratio of (a):(b) ranging from about 2:1 to about 10:1, and
   wherein the composition is essentially anhydrous, comprising no more than 3 wt % water, based on the total weight of the composition.

2. The hair treatment composition of claim 1, wherein the weight ratio of (a):(b) ranges from about 2:1 to about 8:1.

3. The hair treatment composition of claim 1, wherein the composition is free or essentially free of cationic conditioning compounds.

4. The hair treatment composition of claim 1, wherein the composition is free or essentially free of peptides.

5. A hair lightening composition comprising:
   (a) about 1 to about 5 wt % of citric acid and/or a salt thereof;
   (b) about 0.1 to about 2 wt % of glycine and/or a salt thereof;
   (c) optionally, one or more cationic conditioning agents;
   (d) one or more bleaching agents;
   (e) about 1 to about 5 wt % of at least one oil;
   (f) about 0.5 to about 2 wt % of at least one thickening agent; and
   (g) one or more anionic surfactants;
   wherein the composition comprises a total amount of compounds chosen from (a) citric acid and salts thereof and (b) glycine and salts thereof in a weight ratio of (a):(b) ranging from about 2:1 to about 10:1;
   wherein all amounts are based on the total weight of the composition; and
   wherein the composition is essentially anhydrous, comprising no more than 3 wt % water, based on the total weight of the composition.

6. The hair lightening composition of claim 5, wherein the weight ratio of (a):(b) ranges from about 2:1 to about 8:1.

7. The hair lightening composition of claim 5, comprising about 0.6 wt % of compounds chosen from (b) glycine and/or a salt thereof.

8. The hair lightening composition of claim 5, comprising about 3.6 wt % of compounds chosen from (a) citric acid and/or a salt thereof.

9. The hair lightening composition of claim 5, wherein the one or more bleaching agents are selected from the group consisting of one or more peroxides, persulfates, perborates, and percarbonates.

10. The hair lightening composition of claim 9 comprising one or more persulfates selected from the group consisting of sodium persulfate, potassium persulfate, ammonium persulfate, and a mixture thereof.

11. The hair lightening composition of claim 5 comprising:
    (d) about 20 to about 80 wt % of the one or more bleaching agents, based on the total weight of the hair lightening composition.

12. The hair lightening composition of claim 5, wherein the one or more oils comprises mineral oil.

13. The hair lightening composition of claim 5, wherein the one or more thickening agents comprises guar gum.

14. The hair lightening composition of claim 5, comprising at least two thickening agents.

15. The hair lightening composition of claim 5, wherein the composition is free or essentially free of cationic conditioning compounds.

16. The hair lightening composition of claim 5, wherein the composition is free or essentially free of peptides.

17. A hair lightening composition comprising:
    (a) about 0.1 to about 10 wt % of citric acid and/or a salt thereof;
    (b) about 0.01 to about 5 wt % of one or more aliphatic amino acids selected from the group consisting of glycine, alanine, valine, leucine, isoleucine, a salt thereof, and a mixture thereof;
    (d) about 20 to about 80 wt. % of one or more persulfates;
    (e) about 0.1 to about 10 wt % of one or more oils;
    (f) about 0.1 to about 10 wt % of one or more thickening agents;
    (g) about 0.1 to about 10 wt % of one or more anionic surfactants; and
    (h) about 1 to about 40 wt % of one or more alkalizing agents,
    wherein the composition is free or essentially free of cationic conditioning agents;
    wherein all amounts are based on the total weight of the composition; and
    wherein the composition is essentially anhydrous, comprising no more than 3 wt % water, based on the total weight of the hair lightening composition.

18. A kit comprising:
    i. the hair lightening composition of claim 5; and
    ii. an aqueous developer composition comprising one or more peroxides; and
    iii. optionally, a third composition comprising one or more hair conditioning agents and/or one or more direct dyes.

19. A method for lightening hair comprising:
    i. mixing a hair lightening composition of claim 5 with an aqueous developer composition comprising one or more peroxides;
    ii. applying the mixture onto hair and allowing the mixture to remain on the hair for about 1 to about 45 minutes; and
    iii. rinsing the mixture from hair.

* * * * *